US011246661B2

(12) United States Patent
Davies

(10) Patent No.: US 11,246,661 B2
(45) Date of Patent: Feb. 15, 2022

(54) DEVICES SYSTEMS AND METHODS FOR CORONARY INTERVENTION ASSESSMENT, PLANNING, AND TREATMENT BASED ON DESIRED OUTCOME

(71) Applicant: Imperial Innovations Limited, London (GB)

(72) Inventor: Justin Davies, London (GB)

(73) Assignee: IMPERIAL INNOVATIONS LIMITED, London (GB)

( * ) Notice: Subject to any disclaimer, the term of this patent is extended or adjusted under 35 U.S.C. 154(b) by 628 days.

(21) Appl. No.: 15/764,865

(22) PCT Filed: Sep. 28, 2016

(86) PCT No.: PCT/IB2016/055788
§ 371 (c)(1),
(2) Date: Mar. 29, 2018

(87) PCT Pub. No.: WO2017/056007
PCT Pub. Date: Apr. 6, 2017

(65) Prior Publication Data
US 2018/0280088 A1    Oct. 4, 2018

Related U.S. Application Data

(60) Provisional application No. 62/234,441, filed on Sep. 29, 2015.

(51) Int. Cl.
*A61B 34/10* (2016.01)
*A61B 5/0215* (2006.01)
(Continued)

(52) U.S. Cl.
CPC .......... *A61B 34/10* (2016.02); *A61B 5/02007* (2013.01); *A61B 5/02158* (2013.01);
(Continued)

(58) Field of Classification Search
CPC .......... A61B 5/02; A61B 5/007; A61B 5/021; A61B 6/504
See application file for complete search history.

(56) References Cited

U.S. PATENT DOCUMENTS 7,930,014 B2    4/2011    Huennekens et al.
2008/0221442 A1    9/2008    Tolkowsky et al.
(Continued)

FOREIGN PATENT DOCUMENTS

WO    2010058398    5/2010
WO    2012014212    2/2012

*Primary Examiner* — Puya Agahi

(57) ABSTRACT

The present disclosure relates generally to the assessment and treatment of vessels, including for percutaneous coronary intervention (PCI) and coronary artery bypass grafting (CABG). For example, some embodiments of the present disclosure are suited for identifying the available intervention technique(s) suitable to achieve a desired outcome selected or input by a user. For example, in some implementations a method comprises receiving pressure measurements obtained by one or more intravascular pressure-sensing instruments positioned within a vessel of a patient; receiving an input from a user regarding a desired pressure value for the vessel of the patient; identifying an available treatment option based on the received pressure measurements and the desired pressure value; and outputting, to a display device, a screen display including a visual representation of the available treatment option. Related devices and systems are also described.

14 Claims, 12 Drawing Sheets

(51) Int. Cl.
*G16H 50/50* (2018.01)
*A61B 5/00* (2006.01)
*A61B 5/02* (2006.01)
*A61B 17/22* (2006.01)
*G16H 40/20* (2018.01)
*G16H 20/30* (2018.01)
*G16H 10/60* (2018.01)
*G16H 30/20* (2018.01)
*A61B 6/00* (2006.01)
*A61F 2/82* (2013.01)
*A61B 90/00* (2016.01)

(52) U.S. Cl.
CPC ............ *A61B 5/4848* (2013.01); *A61B 5/743* (2013.01); *A61B 6/463* (2013.01); *A61B 6/504* (2013.01); *A61B 6/5247* (2013.01); *A61B 17/22* (2013.01); *A61F 2/82* (2013.01); *G16H 10/60* (2018.01); *G16H 20/30* (2018.01); *G16H 30/20* (2018.01); *G16H 40/20* (2018.01); *G16H 50/50* (2018.01); *A61B 2090/364* (2016.02)

(56) References Cited

U.S. PATENT DOCUMENTS

| | | |
|---|---|---|
| 2010/0125288 A1 | 5/2010 | Gelfand |
| 2012/0041318 A1 | 2/2012 | Taylor |
| 2012/0084064 A1 | 4/2012 | Dzenis et al. |
| 2013/0004619 A1 | 2/2013 | Chow et al. |
| 2013/0046190 A1* | 2/2013 | Davies ............... A61B 5/0215 600/486 |
| 2014/0018792 A1 | 7/2014 | Gang et al. |
| 2014/0187920 A1 | 7/2014 | Millett et al. |
| 2015/0025330 A1 | 1/2015 | Davies |
| 2015/0119705 A1 | 4/2015 | Tochterman et al. |
| 2016/0007866 A1 | 1/2016 | Tochterman et al. |
| 2016/0073972 A1 | 3/2016 | Alpert et al. |

* cited by examiner

DEVICES SYSTEMS AND METHODS FOR CORONARY INTERVENTION ASSESSMENT, PLANNING, AND TREATMENT BASED ON DESIRED OUTCOME

CROSS-REFERENCE TO PRIOR APPLICATIONS

This application is the U.S. National Phase application under 35 U.S.C. § 371 of International Application No. PCT/IB2016/055788, filed on Sep. 28, 2016, which claims the benefit of U.S. Provisional Patent Application No. 62/234,441 filed on Sep. 29, 2015. These applications are hereby incorporated by reference herein.

TECHNICAL FIELD

The present disclosure relates generally to the assessment and treatment of vessels, including for percutaneous coronary intervention (PCI) and coronary artery bypass grafting (CABG). For example, some embodiments of the present disclosure are suited for identifying the available intervention technique(s) suitable to achieve a desired outcome. In some instances, a user selects or inputs one or more parameters of the desired outcome.

BACKGROUND

Innovations in diagnosing and verifying the level of success of treatment of disease have progressed from solely external imaging processes to include internal diagnostic processes. In addition to traditional external image techniques such as X-ray, MRI, CT scans, fluoroscopy, and angiography, small sensors may now be placed directly in the body. For example, diagnostic equipment and processes have been developed for diagnosing vasculature blockages and other vasculature disease by means of ultra-miniature sensors placed upon the distal end of a flexible elongate member such as a catheter, or a guide wire used for catheterization procedures. For example, known medical sensing techniques include intravascular ultrasound (IVUS), forward looking IVUS (FL-IVUS), fractional flow reserve (FFR) determination, a coronary flow reserve (CFR) determination, optical coherence tomography (OCT), transesophageal echocardiography, and image-guided therapy.

One exemplary type of procedure involves pressure measurements within a blood vessel. A currently accepted technique for assessing the severity of a stenosis in the blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment. Another technique for assessing blood vessels utilizes Instant Wave-Free Ratio™ Functionality (iFR® Functionality) (both trademarks of Volcano Corp.), which includes the determination of a pressure ratio across a stenosis during the wave-free period, when resistance is naturally constant and minimized in the cardiac cycle. The iFR modality does not require administration of a hyperemic agent. The normal value of iFR in a healthy vessel is 1.00, while values less than about 0.89 are generally deemed significant and require treatment.

When an occluded blood vessel that requires treatment is identified, a percutaneous coronary intervention (PCI) is a therapeutic procedure that can be utilized to treat the vessel. A PCI includes angioplasty and positioning a stent across the stenosis to open the vessel. Clinicians conventionally rely on angiography and physiologic measurements of pressure and/or flow, which are not meaningfully connected, to plan a therapeutic intervention. Planning the therapeutic intervention can include selecting various parameters related to the stent, such as positioning, length, diameter, etc. Because it is difficult to integrate the various sources of data, there is difficulty in developing the therapeutic plan. Further, there is little ability to predict the efficacy of the therapeutic intervention based on the available data. For example, a clinician conventionally cannot determine, with a clinical certainty that is supported by the collected data, what the effect of changing the positioning and/or length of a stent is on the efficacy of the stent placement.

Accordingly, there remains a need for improved devices, systems, and methods for assessing the severity of a blockage in a vessel and, in particular, a stenosis in a blood vessel. There also remains a need for improved devices, systems, and methods for planning a PCI by connecting the angiography and physiologic data in a way that allows clinicians to efficiently plan and evaluate the proposed therapy. Further, there remains a need for providing visual depictions of a vessel and a proposed therapeutic intervention, such as a stent, in the vessel that allow a clinician to plan, evaluate, and change the proposed therapy in a manner supported by the collected physiologic data.

SUMMARY

Embodiments of the present disclosure are configured to provide devices, systems, and methods for the assessment and treatment of vessels, including for percutaneous coronary intervention (PCI) and coronary artery bypass grafting (CABG), that achieve a desired outcome. In some instances, a user selects or inputs one or more parameters of the desired outcome.

In an exemplary embodiment, a method includes receiving pressure measurements obtained by one or more intravascular pressure-sensing instruments positioned within a vessel of a patient; receiving an input from a user regarding a desired pressure value for the vessel of the patient; identifying an available treatment option based on the received pressure measurements and the desired pressure value; and outputting, to a display device, a screen display including a visual representation of the available treatment option.

In some embodiments, the method further includes receiving angiography data obtained simultaneously with the pressure measurements. The visual representation of the available treatment option can include a graphical overlay on the angiographic image. The received pressure measurements can include proximal pressure measurements and distal pressure measurements and the desired pressure value can be a pressure ratio, such as FFR, iFR, Pd/Pa, compensated Pd/Pa, compensated iFR, or other ratio. In that regard, the pressure ratio can be calculated as a function of the distal pressure measurements relative to the proximal pressure measurements. In some instances, the received pressure measurements are obtained without use of a hyperemic agent. The method can further include receiving an input from the user regarding one or more treatment types to consider for the available treatment option. The one or more treatment types can include at least one of an angioplasty, a stent, a coronary artery bypass graft, or a pharmaceutical. The method can include identifying a stent deployment location within the vessel. The method can also include identifying at least one stent parameter selected from the group consisting of stent length, stent diameter, and stent material.

In some embodiments, the method further includes performing the available treatment option. The method can also include receiving additional pressure measurements obtained by one or more intravascular pressure-sensing instruments positioned within the vessel of the patient after performing the available treatment option. In that regard, the method can determine whether a pressure value based on the additional pressure measurements meets the desired pressure value for the vessel of the patient. For example, the desired pressure value can be a threshold value for a pressure ratio of distal pressure measurements relative to proximal pressure measurements. The method can further include identifying a second available treatment option based on the received additional pressure measurements and the desired pressure value if the pressure value based on the additional pressure measurements does not meet the desired pressure value for the vessel of the patient.

In some embodiments, a system includes a processing system communicatively coupled to one or more intravascular pressure-sensing devices and a display device, the processing system configured to: receive pressure measurements obtained by the one or more intravascular pressure-sensing instruments positioned within a vessel of a patient; receive an input from a user regarding a desired pressure value for the vessel of the patient; identify an available treatment option based on the received pressure measurements and the desired pressure value; and output, to a display device, a screen display including a visual representation of the available treatment option.

In some embodiments, the processing system is further configured to receive angiography data obtained simultaneously with the pressure measurements. The visual representation of the available treatment option can include a graphical overlay on the angiographic image. The received pressure measurements can include proximal pressure measurements and distal pressure measurements and the desired pressure value can be a pressure ratio, such as FFR, iFR, Pd/Pa, compensated Pd/Pa, compensated iFR, or other ratio. The pressure ratio can be calculated as a function of the distal pressure measurements relative to the proximal pressure measurements. In some instances, the received pressure measurements are obtained without use of a hyperemic agent.

The processing system can be further configured to receive an input from the user regarding one or more treatment types to consider for the available treatment option. In some implementations, the one or more treatment types include at least one of an angioplasty, a stent, a coronary artery bypass graft, or a pharmaceutical. The processing system can be configured to identify the available treatment option by identifying a stent deployment location within the vessel. The processing system can also be configured to identify the available treatment option by identifying at least one stent parameter selected from the group consisting of stent length, stent diameter, and stent material.

In some instances, the processing system can be configured to receive additional pressure measurements obtained by one or more intravascular pressure-sensing instruments positioned within the vessel of the patient after performance of the available treatment option. The processing system can be configured to determine whether a pressure value based on the additional pressure measurements meets the desired pressure value for the vessel of the patient. In some instances, the desired pressure value is a threshold value for a pressure ratio of distal pressure measurements relative to proximal pressure measurements. The processing system can also be configured to identify a second available treatment option based on the received additional pressure measurements and the desired pressure value if the pressure value based on the additional pressure measurements does not meet the desired pressure value for the vessel of the patient. In some instances, the system further includes the one or more intravascular pressure-sensing devices.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
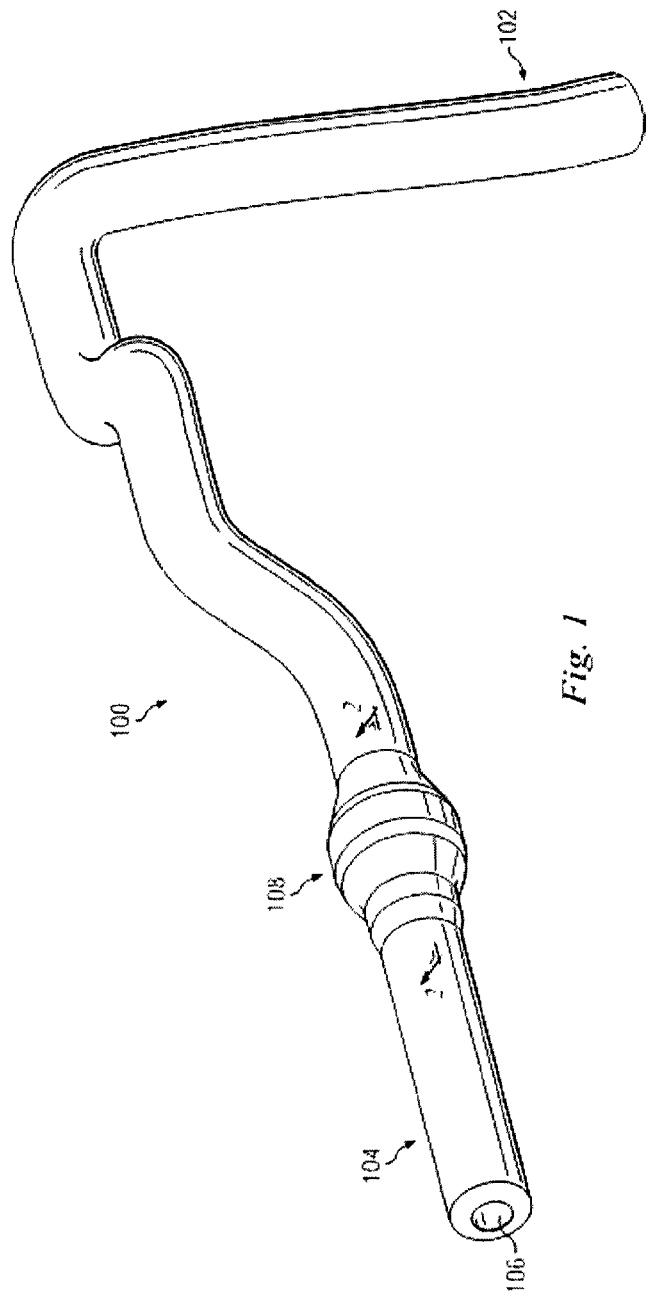
FIG. 1 is a diagrammatic perspective view of a vessel having a stenosis according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 2:
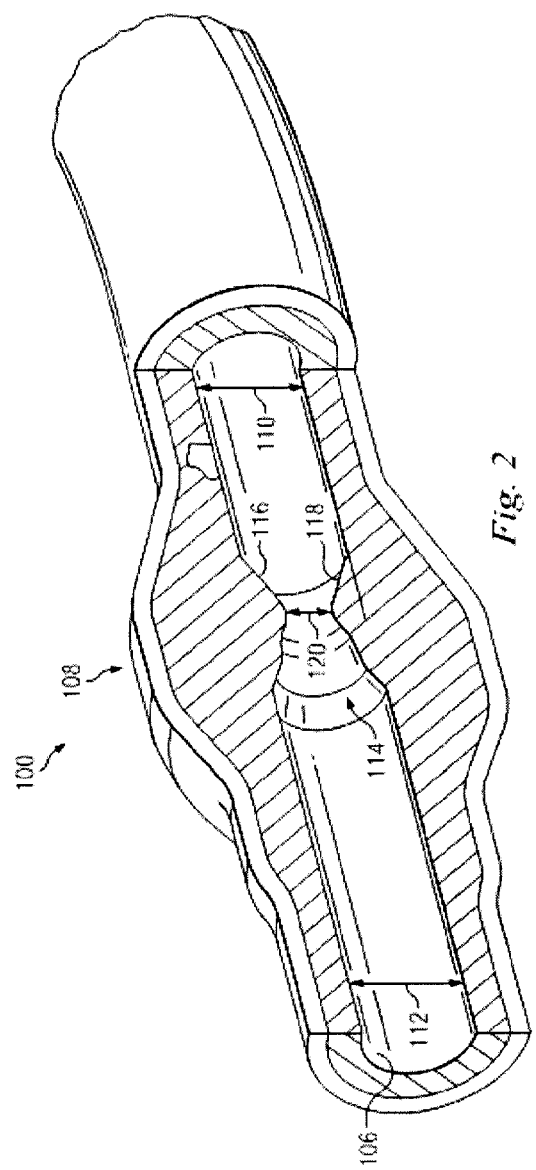
FIG. 2 is a diagrammatic, partial cross-sectional perspective view of a portion of the vessel of FIG. 1 taken along section line 2-2 of FIG. 1.

Referring to FIGS. 1 and 2, shown therein is a vessel 100 having a stenosis according to an embodiment of the present disclosure. In that regard, FIG. 1 is a diagrammatic perspective view of the vessel 100, while FIG. 2 is a partial cross-sectional perspective view of a portion of the vessel 100 taken along section line 2-2 of FIG. 1. Referring more specifically to FIG. 1, the vessel 100 includes a proximal portion 102 and a distal portion 104. A lumen 106 extends along the length of the vessel 100 between the proximal portion 102 and the distal portion 104. In that regard, the lumen 106 is configured to allow the flow of fluid through the vessel. In some instances, the vessel 100 is a blood vessel. In some particular instances, the vessel 100 is a coronary artery. In such instances, the lumen 106 is configured to facilitate the flow of blood through the vessel 100.

As shown, the vessel 100 includes a stenosis 108 between the proximal portion 102 and the distal portion 104. Stenosis 108 is generally representative of any blockage or other structural arrangement that results in a restriction to the flow of fluid through the lumen 106 of the vessel 100. Embodiments of the present disclosure are suitable for use in a wide variety of vascular applications, including without limitation coronary, peripheral (including but not limited to lower limb, carotid, and neurovascular), renal, and/or venous. Where the vessel 100 is a blood vessel, the stenosis 108 may be a result of plaque buildup, including without limitation plaque components such as fibrous, fibro-lipidic (fibro fatty), necrotic core, calcified (dense calcium), blood, fresh thrombus, and mature thrombus. Generally, the composition of the stenosis will depend on the type of vessel being evaluated. In that regard, it is understood that the concepts of the present disclosure are applicable to virtually any type of blockage or other narrowing of a vessel that results in decreased fluid flow.

Referring more particularly to FIG. 2, the lumen 106 of the vessel 100 has a diameter 110 proximal of the stenosis 108 and a diameter 112 distal of the stenosis. In some instances, the diameters 110 and 112 are substantially equal to one another. In that regard, the diameters 110 and 112 are intended to represent healthy portions, or at least healthier portions, of the lumen 106 in comparison to stenosis 108. Accordingly, these healthier portions of the lumen 106 are illustrated as having a substantially constant cylindrical profile and, as a result, the height or width of the lumen has been referred to as a diameter. However, it is understood that in many instances these portions of the lumen 106 will also have plaque buildup, a non-symmetric profile, and/or other irregularities, but to a lesser extent than stenosis 108 and, therefore, will not have a cylindrical profile. In such instances, the diameters 110 and 112 are understood to be representative of a relative size or cross-sectional area of the lumen and do not imply a circular cross-sectional profile.

As shown in FIG. 2, stenosis 108 includes plaque buildup 114 that narrows the lumen 106 of the vessel 100. In some instances, the plaque buildup 114 does not have a uniform or symmetrical profile, making angiographic evaluation of such a stenosis unreliable. In the illustrated embodiment, the plaque buildup 114 includes an upper portion 116 and an opposing lower portion 118. In that regard, the lower portion 118 has an increased thickness relative to the upper portion 116 that results in a non-symmetrical and non-uniform profile relative to the portions of the lumen proximal and distal of the stenosis 108. As shown, the plaque buildup 114 decreases the available space for fluid to flow through the lumen 106. In particular, the cross-sectional area of the lumen 106 is decreased by the plaque buildup 114. At the narrowest point between the upper and lower portions 116, 118 the lumen 106 has a height 120, which is representative of a reduced size or cross-sectional area relative to the diameters 110 and 112 proximal and distal of the stenosis 108. Note that the stenosis 108, including plaque buildup 114 is exemplary in nature and should be considered limiting in any way. In that regard, it is understood that the stenosis 108 has other shapes and/or compositions that limit the flow of fluid through the lumen 106 in other instances. While the vessel 100 is illustrated in FIGS. 1 and 2 as having a single stenosis 108 and the description of the embodiments below is primarily made in the context of a single stenosis, it is nevertheless understood that the devices, systems, and methods described herein have similar application for a vessel having multiple stenosis regions.

Figure 3:
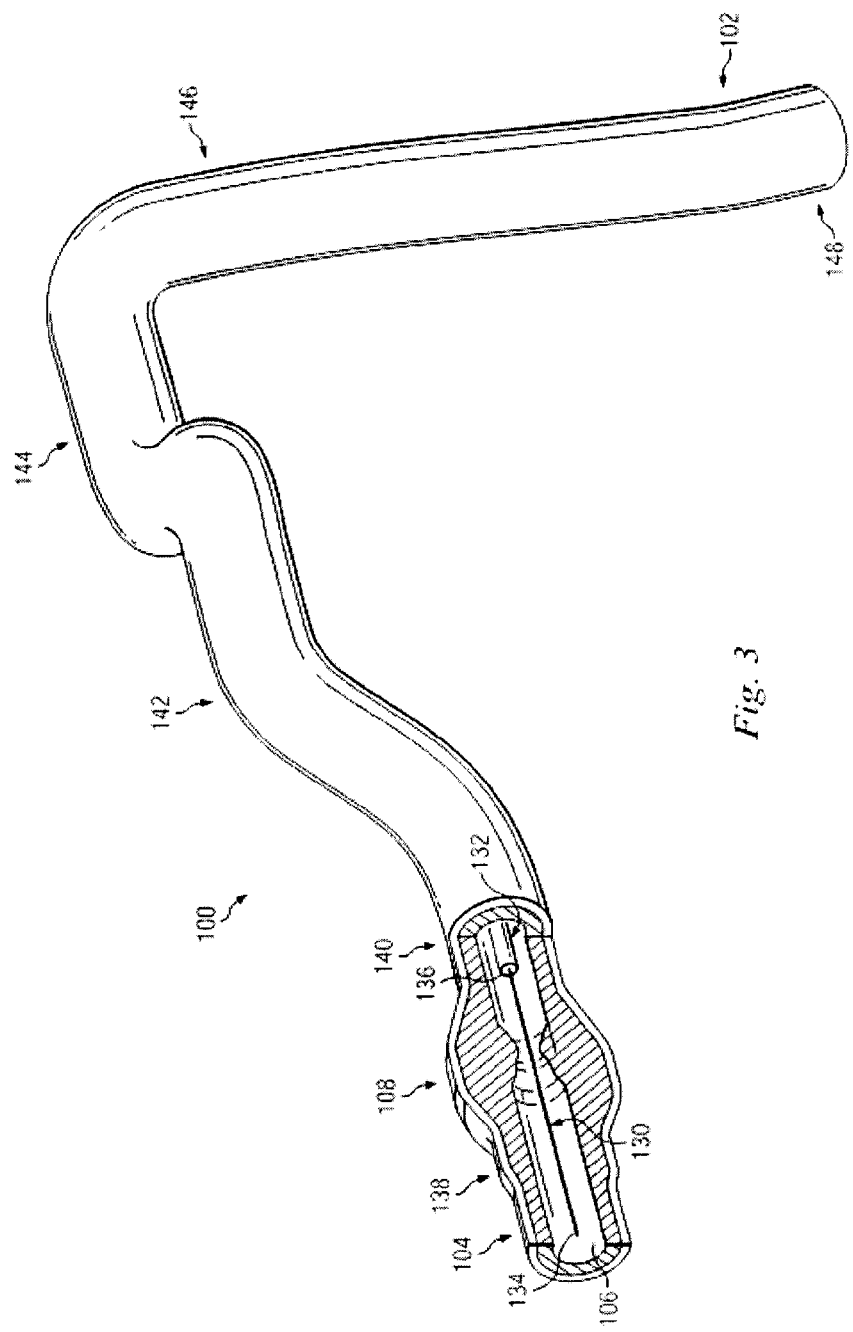
FIG. 3 is a diagrammatic, partial cross-sectional perspective view of the vessel of FIGS. 1 and 2 with instruments positioned therein according to an embodiment of the present disclosure.

Referring now to FIG. 3, the vessel 100 is shown with instruments 130 and 132 positioned therein according to an embodiment of the present disclosure. In general, instruments 130 and 132 may be any form of device, instrument, or probe sized and shaped to be positioned within a vessel. In the illustrated embodiment, instrument 130 is generally representative of a guide wire, while instrument 132 is generally representative of a catheter. In that regard, instrument 130 extends through a central lumen of instrument 132. However, in other embodiments, the instruments 130 and 132 take other forms. In that regard, the instruments 130 and 132 are of similar form in some embodiments. For example, in some instances, both instruments 130 and 132 are guide wires. In other instances, both instruments 130 and 132 are catheters. On the other hand, the instruments 130 and 132 are of different form in some embodiments, such as the illustrated embodiment, where one of the instruments is a catheter and the other is a guide wire. Further, in some instances, the instruments 130 and 132 are disposed coaxial with one another, as shown in the illustrated embodiment of FIG. 3. In other instances, one of the instruments extends through an off-center lumen of the other instrument. In yet other instances, the instruments 130 and 132 extend side-by-side. In some particular embodiments, at least one of the instruments is as a rapid-exchange device, such as a rapid-exchange catheter. In such embodiments, the other instrument is a buddy wire or other device configured to facilitate the introduction and removal of the rapid-exchange device. Further still, in other instances, instead of two separate instruments 130 and 132 a single instrument is utilized. In some embodiments, the single instrument incorporates aspects of the functionalities (e.g., data acquisition) of both instruments 130 and 132.

Instrument 130 is configured to obtain diagnostic information about the vessel 100. In that regard, the instrument 130 includes one or more sensors, transducers, and/or other monitoring elements configured to obtain the diagnostic information about the vessel. The diagnostic information includes one or more of pressure, flow (velocity and/or volume), images (including images obtained using ultrasound (e.g., IVUS), OCT, thermal, and/or other imaging techniques), temperature, and/or combinations thereof. The one or more sensors, transducers, and/or other monitoring elements are positioned adjacent a distal portion of the instrument 130 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 134 of the instrument 130 in some instances. In some instances, at least one of the one or more sensors, transducers, and/or other monitoring elements is positioned at the distal tip of the instrument 130.

The instrument 130 includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Examples of commercially available guide wire products that include suitable pressure monitoring elements include, without limitation, the Verrata® pressure guide wire, the PrimeWire Prestige® PLUS pressure guide wire, and the ComboWire® XT pressure and flow guide wire, each available from Volcano Corporation, as well as the PressureWire™ Certus guide wire and the PressureWire™ Aeris guide wire, each available from St. Jude Medical, Inc. Generally, the instrument 130 is sized such that it can be positioned through the stenosis 108 without significantly impacting fluid flow across the stenosis, which would impact the distal pressure reading. Accordingly, in some instances the instrument 130 has an outer diameter of 0.018" or less. In some embodiments, the instrument 130 has an outer diameter of 0.014" or less. In some embodiments, the instrument 130 has an outer diameter of 0.035" or less.

Instrument 132 is also configured to obtain diagnostic information about the vessel 100. In some instances, instrument 132 is configured to obtain the same diagnostic information as instrument 130. In other instances, instrument 132 is configured to obtain different diagnostic information than instrument 130, which may include additional diagnostic information, less diagnostic information, and/or alternative diagnostic information. The diagnostic information obtained by instrument 132 includes one or more of pressure, flow (velocity and/or volume), images (including images obtained using ultrasound (e.g., IVUS), OCT, thermal, and/or other imaging techniques, temperature, and/or combinations thereof. Instrument 132 includes one or more sensors, transducers, and/or other monitoring elements configured to obtain this diagnostic information. In that regard, the one or more sensors, transducers, and/or other monitoring elements are positioned adjacent a distal portion of the instrument 132 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 136 of the instrument 132 in some instances. In some instances, at least one of the one or more sensors, transducers, and/or other monitoring elements is positioned at the distal tip of the instrument 132.

Similar to instrument 130, instrument 132 also includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Currently available catheter products suitable for use with one or more of Siemens AXIOM Sensis, Mennen Horizon XVu, and Philips Xper IM Physiomonitoring 5 and include pressure monitoring elements can be utilized for instrument 132 in some instances.

In accordance with aspects of the present disclosure, at least one of the instruments 130 and 132 is configured to monitor a pressure within the vessel 100 distal of the stenosis 108 and at least one of the instruments 130 and 132 is configured to monitor a pressure within the vessel proximal of the stenosis. In that regard, the instruments 130, 132 are sized and shaped to allow positioning of the at least one element configured to monitor pressure within the vessel 100 to be positioned proximal and/or distal of the stenosis 108 as necessary based on the configuration of the devices. In that regard, FIG. 3 illustrates a position 138 suitable for measuring pressure distal of the stenosis 108. In that regard, the position 138 is less than 5 cm, less than 3 cm, less than 2 cm, less than 1 cm, less than 5 mm, and/or less than 2.5 mm from the distal end of the stenosis 108 (as shown in FIG. 2) in some instances. FIG. 3 also illustrates a plurality of suitable positions for measuring pressure proximal of the stenosis 108. In that regard, positions 140, 142, 144, 146, and 148 each represent a position that is suitable for monitoring the pressure proximal of the stenosis in some instances. In that regard, the positions 140, 142, 144, 146, and 148 are positioned at varying distances from the proximal end of the stenosis 108 ranging from more than 20 cm down to about 5 mm or less. Generally, the proximal pressure measurement will be spaced from the proximal end of the stenosis. Accordingly, in some instances, the proximal pressure measurement is taken at a distance equal to or greater than an inner diameter of the lumen of the vessel from the proximal end of the stenosis. In the context of coronary artery pressure measurements, the proximal pressure measurement is generally taken at a position proximal of the stenosis and distal of the aorta, within a proximal portion of the vessel. However, in some particular instances of coronary artery pressure measurements, the proximal pressure measurement is taken from a location inside the aorta. In other instances, the proximal pressure measurement is taken at the root or ostium of the coronary artery.

In some embodiments, at least one of the instruments 130 and 132 is configured to monitor pressure within the vessel 100 while being moved through the lumen 106. In some instances, instrument 130 is configured to be moved through the lumen 106 and across the stenosis 108. In that regard, the instrument 130 is positioned distal of the stenosis 108 and moved proximally (i.e., pulled back) across the stenosis to a position proximal of the stenosis in some instances. In other instances, the instrument 130 is positioned proximal of the stenosis 108 and moved distally across the stenosis to a position distal of the stenosis. Movement of the instrument 130, either proximally or distally, is controlled manually by medical personnel (e.g., hand of a surgeon) in some embodiments. In other embodiments, movement of the instrument 130, either proximally or distally, is controlled automatically by a movement control device (e.g., a pullback device, such as the Trak Back® II Device available from Volcano Corporation). In that regard, the movement control device controls the movement of the instrument 130 at a selectable and known speed (e.g., 2.0 mm/s, 1.0 mm/s, 0.5 mm/s, 0.2 mm/s, etc.) in some instances. Movement of the instrument 130 through the vessel is continuous for each pullback or push through, in some instances. In other instances, the instrument 130 is moved step-wise through the vessel (i.e., repeatedly moved a fixed amount of distance and/or a fixed amount of time). Some aspects of the visual depictions discussed below are particularly suited for embodiments where at least one of the instruments 130 and 132 is moved through the lumen 106. Further, in some particular instances, aspects of the visual depictions discussed below are particularly suited for embodiments where a single instrument is moved through the lumen 106, with or without the presence of a second instrument.

The instruments 130 and/or 132 can be used to conduct medical sensing procedures associated with Instant Wave-Free Ratio™ Functionality (iFR® Functionality) (both trademarks of Volcano Corp.) and those disclosed in U.S. patent application Ser. No. 13/460,296, entitled "DEVICES, SYSTEMS, AND METHODS FOR ASSESSING A VESSEL," hereby incorporated by reference in its entirety, which discloses the use of pressure ratios that are available without application of a hyperemic agent. Further, medical sensing procedures associated with compensated Pd/Pa ratios suitable for estimating iFR®, FFR, and/or other accepted diagnostic pressure ratios as disclosed in U.S. Provisional Patent Application No. 62/024,005, filed Jul. 14, 2014 and entitled "DEVICES, SYSTEMS, AND METHODS FOR TREATMENT OF VESSELS," which is hereby incorporated by reference in its entirety, can be conducted using the instruments 130 and/or 132.

Figure 4:
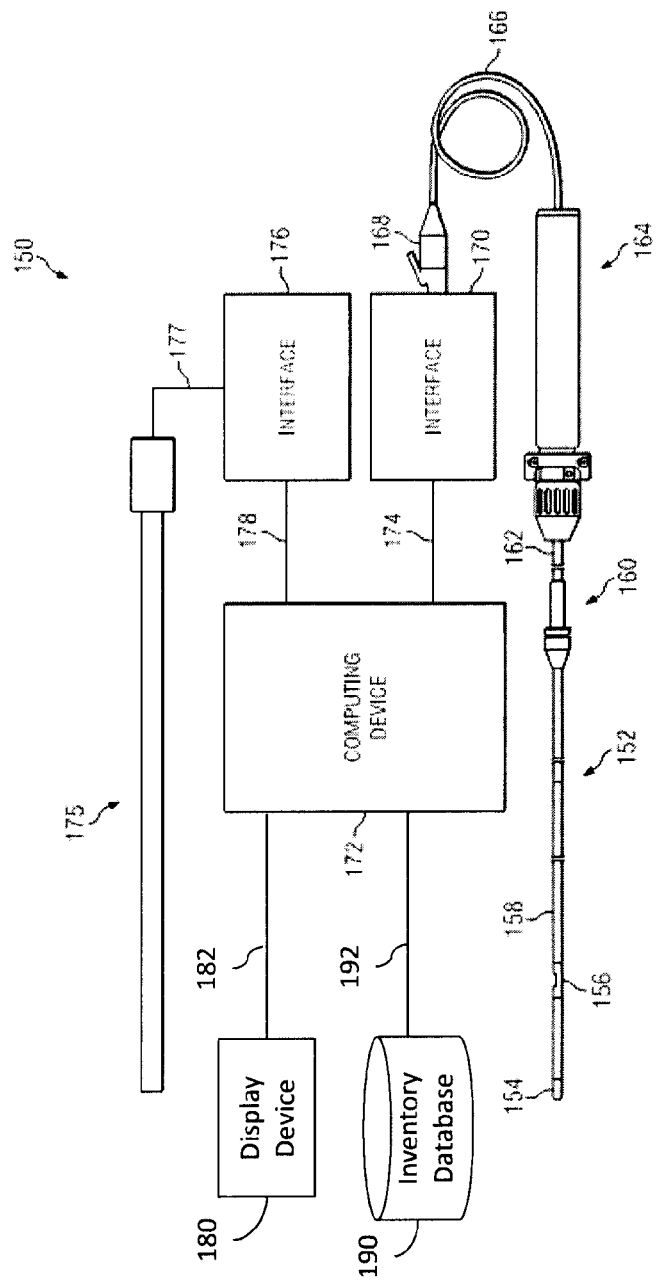
FIG. 4 is a diagrammatic, schematic view of a system according to an embodiment of the present disclosure.

Referring now to FIG. 4, shown therein is a system 150 according to an embodiment of the present disclosure. In that regard, FIG. 4 is a diagrammatic, schematic view of the system 150. As shown, the system 150 includes an instrument 152. In that regard, in some instances instrument 152 is suitable for use as at least one of instruments 130 and 132 discussed above. Accordingly, in some instances the instrument 152 includes features similar to those discussed above with respect to instruments 130 and 132 in some instances. In the illustrated embodiment, the instrument 152 is a guide wire having a distal portion 154 and a housing 156 positioned adjacent the distal portion. In that regard, the housing 156 is spaced approximately 3 cm from a distal tip of the instrument 152. The housing 156 is configured to house one or more sensors, transducers, and/or other monitoring elements configured to obtain the diagnostic information about the vessel. In the illustrated embodiment, the housing 156 contains at least a pressure sensor configured to monitor a pressure within a lumen in which the instrument 152 is positioned. A shaft 158 extends proximally from the housing 156. A torque device 160 is positioned over and coupled to a proximal portion of the shaft 158. A proximal end portion 162 of the instrument 152 is coupled to a connector 164. A cable 166 extends from connector 164 to a connector 168. In some instances, connector 168 is configured to be plugged into an interface 170. In that regard, interface 170 is a patient interface module (PIM) in some instances. In some instances, the cable 166 is replaced with a wireless connection. In that regard, it is understood that various communication pathways between the instrument 152 and the interface 170 may be utilized, including physical connections (including electrical, optical, and/or fluid connections), wireless connections, and/or combinations thereof.

The interface 170 is communicatively coupled to a computing device 172 via a connection 174. Computing device 172 is generally representative of any device suitable for performing the processing and analysis techniques discussed within the present disclosure. In some embodiments, the computing device 172 includes a processor, random access memory, and a storage medium. In that regard, in some particular instances the computing device 172 is programmed to execute steps associated with the data acquisition and analysis described herein. Accordingly, it is understood that any steps related to data acquisition, data processing, instrument control, and/or other processing or control aspects of the present disclosure may be implemented by the computing device using corresponding instructions stored on or in a non-transitory computer readable medium accessible by the computing device. In some instances, the computing device 172 is a console device. In some particular instances, the computing device 172 is similar to the s5™ Imaging System or the s5i® Imaging System, each available from Volcano Corporation. In some instances, the computing device 172 is portable (e.g., handheld, on a rolling cart, etc.). In some instances, all or a portion of the computing device 172 can be implemented as a bedside controller such that one or more processing steps described herein can be performed by processing component(s) of the bedside controller. An exemplary bedside controller is described in U.S. Provisional Application No. 62/049,265, titled "Bedside Controller for Assessment of Vessels and Associated Devices, Systems, and Methods," and filed Sep. 11, 2014, the entirety of which is hereby incorporated by reference herein. Further, it is understood that in some instances the computing device 172 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

Together, connector 164, cable 166, connector 168, interface 170, and connection 174 facilitate communication between the one or more sensors, transducers, and/or other monitoring elements of the instrument 152 and the computing device 172. However, this communication pathway is exemplary in nature and should not be considered limiting in any way. In that regard, it is understood that any communication pathway between the instrument 152 and the computing device 172 may be utilized, including physical connections (including electrical, optical, and/or fluid connections), wireless connections, and/or combinations thereof. In that regard, it is understood that the connection 174 is wireless in some instances. In some instances, the connection 174 includes a communication link over a network (e.g., intranet, internet, telecommunications network, and/or other network). In that regard, it is understood that the computing device 172 is positioned remote from an operating area where the instrument 152 is being used in some instances. Having the connection 174 include a connection over a network can facilitate communication between the instrument 152 and the remote computing device 172 regardless of whether the computing device is in an adjacent room, an adjacent building, or in a different state/country. Further, it is understood that the communication pathway between the instrument 152 and the computing device 172 is a secure connection in some instances. Further still, it is understood that, in some instances, the data communicated over one or more portions of the communication pathway between the instrument 152 and the computing device 172 is encrypted.

The system 150 also includes an instrument 175. In that regard, in some instances instrument 175 is suitable for use as at least one of instruments 130 and 132 discussed above. Accordingly, in some instances the instrument 175 includes features similar to those discussed above with respect to instruments 130 and 132 in some instances. In the illustrated embodiment, the instrument 175 is a catheter-type device. In that regard, the instrument 175 includes one or more sensors, transducers, and/or other monitoring elements adjacent a distal portion of the instrument configured to obtain the diagnostic information about the vessel. In the illustrated embodiment, the instrument 175 includes a pressure sensor configured to monitor a pressure within a lumen in which the instrument 175 is positioned. The instrument 175 is in communication with an interface 176 via connection 177. In some instances, interface 176 is a hemodynamic monitoring system or other control device, such as Siemens AXIOM Sensis, Mennen Horizon XVu, and Philips Xper IM Physiomonitoring 5. In one particular embodiment, instrument 175 is a pressure-sensing catheter that includes fluid column extending along its length. In such an embodiment, interface 176 includes a hemostasis valve fluidly coupled to the fluid column of the catheter, a manifold fluidly coupled to the hemostasis valve, and tubing extending between the components as necessary to fluidly couple the components. In that regard, the fluid column of the catheter is in fluid communication with a pressure sensor via the valve, manifold, and tubing. In some instances, the pressure sensor is part of interface 176. In other instances, the pressure sensor is a separate component positioned between the instrument 175 and the interface 176. The interface 176 is communicatively coupled to the computing device 172 via a connection 178.

The computing device 172 is communicatively coupled to a display device 180 via a connection 182. In some embodiments, the display device 172 is a component of the computing device 172, while in other embodiments, the display device 172 is distinct from the computing device 172. In some embodiments, the display device 172 is implemented as a bedside controller having a touch-screen display as described, for example, in U.S. Provisional Application No. 62/049,265, titled "Bedside Controller for Assessment of Vessels and Associated Devices, Systems, and Methods," and filed Sep. 11, 2014, the entirety of which is hereby incorporated by reference herein. The computing device 172 can generate screen displays including data collected by the instruments 152 and 175 and other instruments, quantities computed based on the collected data, visualizations of the vessel in which the data is collected, and visualizations based on the collected data and computed quantities. Exemplary screen displays are illustrated in FIGS. 7-28. The computing device 172 can provide the display data associated with the screen displays to the display device 180.

The computing device 172 can additionally be communicatively coupled to a user interface device. The user interface device permits a user to interact with the screen displays on the display device 180. For example, the user can provide a user input to modify all or a portion of the screen display using the user interface device. Exemplary user inputs and the corresponding modifications to the screen display are illustrated in FIGS. 7-28. In some embodiments, the user interface device is a separate component from the display device 180. In other embodiments, the user interface device is part of the display device 180. For example, the user interface device can be implemented as a bedside controller having a touch-screen display as described, for example, in U.S. Provisional Application No. 62/049,265, titled "Bedside Controller for Assessment of Vessels and Associated Devices, Systems, and Methods," and filed Sep. 11, 2014, the entirety of which is hereby incorporated by reference herein. In such embodiments, a user input can be a touch input received on the touch sensitive display of the bedside controller.

Similar to the connections between instrument 152 and the computing device 172, interface 176 and connections 177 and 178 facilitate communication between the one or more sensors, transducers, and/or other monitoring elements of the instrument 175 and the computing device 172. However, this communication pathway is exemplary in nature and should not be considered limiting in any way. In that regard, it is understood that any communication pathway between the instrument 175 and the computing device 172 may be utilized, including physical connections (including electrical, optical, and/or fluid connections), wireless connections, and/or combinations thereof. In that regard, it is understood that the connection 178 is wireless in some instances. In some instances, the connection 178 includes a communication link over a network (e.g., intranet, internet, telecommunications network, and/or other network). In that regard, it is understood that the computing device 172 is positioned remote from an operating area where the instrument 175 is being used in some instances. Having the connection 178 include a connection over a network can facilitate communication between the instrument 175 and the remote computing device 172 regardless of whether the computing device is in an adjacent room, an adjacent building, or in a different state/country. Further, it is understood that the communication pathway between the instrument 175 and the computing device 172 is a secure connection in some instances. Further still, it is understood that, in some instances, the data communicated over one or more portions of the communication pathway between the instrument 175 and the computing device 172 is encrypted.

It is understood that one or more components of the system 150 are not included, are implemented in a different arrangement/order, and/or are replaced with an alternative device/mechanism in other embodiments of the present disclosure. For example, in some instances, the system 150 does not include interface 170 and/or interface 176. In such instances, the connector 168 (or other similar connector in communication with instrument 152 or instrument 175) may plug into a port associated with computing device 172. Alternatively, the instruments 152, 175 may communicate wirelessly with the computing device 172. Generally speaking, the communication pathway between either or both of the instruments 152, 175 and the computing device 172 may have no intermediate nodes (i.e., a direct connection), one intermediate node between the instrument and the computing device, or a plurality of intermediate nodes between the instrument and the computing device.

In some embodiments, the system 150 can additionally include a bedside controller, such as the bedside controller described in U.S. Provisional Application No. 62/049,265, titled "Bedside Controller for Assessment of Vessels and Associated Devices, Systems, and Methods," and filed Sep. 11, 2014, the entirety of which is hereby incorporated by reference herein. The bedside controller may be utilized by a clinician to control instruments 152 and 175 to acquire pressure data during a procedure, watch real-time medical pressure measurements (e.g., visual representations of pressure data, such as pressure waveforms, numerical values, etc.), compute pressure ratio(s) based on the collected pressure data, and interact with the obtained medical sensing data, a visual representation of the obtained medical sensing data and/or computed pressure ratio(s), a visualization based on the obtained medical sensing data and/or computed pressure ratio(s), and/or a visual representation of the vessel 100. In that regard, the bedside controller can be communicatively coupled to the computing device 172, the interfaces 170 and 176, and/or the instruments 152 and 175.

In some embodiments, the system 150 can include an inventory database 190 associated with a clinical environment, such as a hospital or other healthcare facility at which a treatment would be carried out on a patient. The inventory database can store various data about the treatment options that are available to a clinician for use at the healthcare facility based on medical equipment, inventory, operating room and/or catheter lab availability, staff availability, etc. For example, in some instances the data can include information about the coronary stents available to the clinician, including such information as manufacturer names, length, diameter, material(s), quantity available, quantity available for immediate use, resupply frequency, next shipment date, treatment outcomes for various patient types, and other suitable information. As described below, the computing device 172 can compile a plurality of available treatment options based on the inventory database 190 and a desired outcome input/selected by the clinician via a user interface. In some instances, the desired outcome is a threshold and/or target value for a pressure measurement, such as a pressure ratio (FFR, iFR, Pd/Pa, etc.) or pressure measurement (e.g., Pd, etc.). The computing device 172 can automatically recommend a particular treatment (e.g., performing angioplasty and deploying a stent from a particular manufacturer, with a particular length, diameter, and/or material, at particular location(s) within the vessel) by performing treatment planning using pressure measurements, flow measurements, angiography images, and/or other diagnostic information about the patient. The computing device 172 can also receive a user input selecting particular treatment options for consideration (or to be excluded from consideration), which may be based on clinician preference or other factors. The computing device 172 is communicatively coupled to the inventory database 190 via a connection 192. The connection 192 can be representative of one or more network connections that communicatively couple the computing device 172 with a computing system of the healthcare facility.

Diagnostic information within a vasculature of interest can be obtained using one or more of instruments 130, 132, 152, and 175. For example, diagnostic information is obtained for one or more coronaries arteries, peripheral arteries, cerebrovascular vessels, etc. The diagnostic information can include pressure-related values, flow-related values, etc. Pressure-related values can include FFR (e.g., a pressure ratio value calculated as a first instrument is moved through a vessel relative to a second instrument, including across at least one stenosis of the vessel), Pd/Pa (e.g., a ratio of the pressure distal to a lesion to the pressure proximal to the lesion), iFR (e.g., a pressure ratio value calculated using a diagnostic window relative to a distance as a first instrument is moved through a vessel relative to a second instrument, including across at least one stenosis of the vessel), etc. Flow-related values can include coronary flow reserve or CFR (e.g., maximum increase in blood flow through the coronary arteries above the normal resting volume), basal stenosis resistance index (BSR), etc.

The diagnostic information and/or data obtained by instruments 130, 132, 152, and/or 175 are correlated or co-registered to angiographic image(s) and/or other two-dimensional or three-dimensional depictions of a patient's vasculature obtained by an external imaging system. In various embodiments, the diagnostic information obtained by the external imaging system can include externally-obtained angiographic images, x-ray images, CT images, PET images, MRI images, SPECT images, and/or other two-dimensional or three-dimensional extraluminal depictions of a patient's vasculature. Spatial co-registration can be completed using techniques disclosed in U.S. Pat. No. 7,930,014, titled "VASCULAR IMAGE CO-REGISTRATION," which is hereby incorporated by reference in its entirety, based on the known pullback speed/distance, based on a known starting point, based on a known ending point, and/or combinations thereof. For example, a mechanical pullback device can be used to conduct the pressure-sensing procedure. The mechanical pullback device can move the pressure-sensing device through the vessel at a fixed, known rate. The location of the pressure measurements and/or the pressure ratio(s) can be determined based on the rate of the pullback and a known location of the pressure-sensing device (e.g., a start position, a mid-point position, an end position, available from angiography data). In some embodiments, diagnostic information and/or data is correlated to vessel images using techniques similar to those described in U.S. Provisional Patent Application No. 61/747,480, titled "SPATIAL CORRELATION OF INTRAVASCULAR IMAGES AND PHYSIOLOGICAL FEATURES" and filed Dec. 31, 2012, which is hereby incorporated by reference in its entirety. In some embodiments, co-registration and/or correlation can be completed as described in U.S. Provisional Patent Application No. 61/856,509, titled "DEVICES, SYSTEMS, AND METHODS FOR ASSESSMENT OF VESSELS" and filed Jul. 19, 2013, which is hereby incorporated by reference in its entirety.

In some embodiments, diagnostic information and/or data is correlated to vessel images using techniques similar to those described in U.S. patent application Ser. No. 14/144,280, titled "DEVICES, SYSTEMS, AND METHODS FOR ASSESSMENT OF VESSELS" and filed Dec. 31, 2012, which is hereby incorporated by reference in its entirety. In some embodiments, co-registration and/or correlation can be completed as described in U.S. Provisional Patent Application No. 61/856,509, titled "DEVICES, SYSTEMS, AND METHODS FOR ASSESSMENT OF VESSELS" and filed Jul. 19, 2013, which is hereby incorporated by reference in its entirety. In other embodiments, co-registration and/or correlation can be completed as described in International Application No. PCT/IL2011/000612, titled "CO-USE OF ENDOLUMINAL DATA AND EXTRALUMINAL IMAGING" and filed Jul. 28, 2011, which is hereby incorporated by reference in its entirety. Further, in some embodiments, co-registration and/or correlation can be completed as described in International Application No. PCT/IL2009/001089, titled "IMAGE PROCESSING AND TOOL ACTUATION FOR MEDICAL PROCEDURES" and filed Nov. 18, 2009, which is hereby incorporated by reference in its entirety. Additionally, in other embodiments, co-registration and/or correlation can be completed as described in U.S. patent application Ser. No. 12/075,244, titled "IMAGING FOR USE WITH MOVING ORGANS" and filed Mar. 10, 2008, which is hereby incorporated by reference in its entirety.

Figure 5:
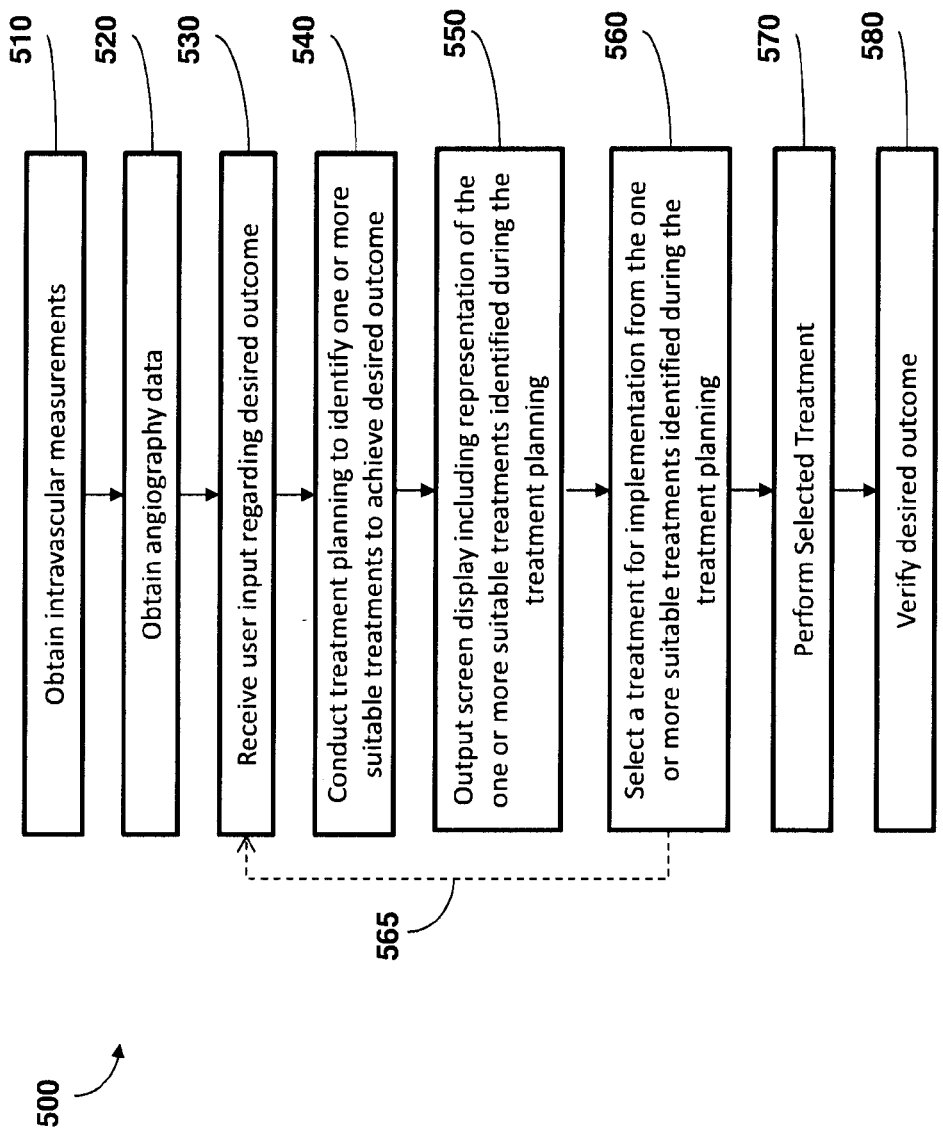
FIG. 5 is a flow diagram of a method of evaluating and treating a vessel of a patient according to an embodiment of the present disclosure.

FIG. 5 is flowchart illustrating a method 500 of evaluating a vessel of a patient. The method 500 will be described in the context of a pressure-sensing procedure, such as an iFR, Pd/Pa, or FFR procedure. It is understood that the method 500 can be carried out in the context of a flow-sensing procedure, such as a CFR procedure. The method 500 can be better understood with reference to FIGS. 6-12. In that regard, the user interface displays of FIGS. 6-12 can be displayed on a display device of system assessing a patient's vasculature, such as the display device 180 associated with computing device 172 (FIG. 4). That is, one or more components (e.g., a processor and/or processing circuit) of the system (e.g., computing device 172) can provide display data to cause the interfaces of FIGS. 6-12 to be shown on a display device (e.g., display device 180). It is understood that the aspects of FIGS. 6-12 may be shown alone or along with other data, images, and/or other information about the patient/vessel(s) of interest.

At block 510, the method 500 includes obtaining intravascular measurements, such as pressure and/or flow measurements. At block 520, the method 500 includes acquiring angiography data. In some embodiments, the pressure measurements are obtained simultaneously as the angiography data is acquired. Simultaneously collecting pressure measurements and angiography data can facilitate co-registration, as described above. For example, the collected pressure data can be co-registered such that the location of the pressure sensing component of the intravascular device within the vessel is known. A processing system can associate the location with the pressure measurements and/or the pressure ratio(s) at that location. The processing system can also generate a screen display including the pressure measurements and/or pressure ratios at their associated locations, as described below with respect to FIGS. 6-8.

To facilitate obtaining the pressure measurements, a clinician can insert pressure-sensing intravascular device(s), such as a catheter or guidewire, into the patient. In some embodiments, the clinician may guide the intravascular device within the patient to a desired position using the angiography data. After the pressure sensing intravascular device has been appropriately positioned in the patient, the clinician can initiate collection of pressure measurements. Pressure measurements can be collected during one or more of the following procedures: an FFR "spot" measurement where the pressure sensor stays in one place while hyperemia is induced; an FFR pullback in which an elongated period of hyperemia is induced and the sensor is pulled back to the ostium; an iFR "spot" measurement that is similar to the FFR spot measurement but without hyperemia; and an iFR pullback which is that the FFR pullback but without hyperemia. In various embodiments, physiological measurement collection can be carried through a combination of one or more of the procedures described above. Physiological measurement can be continuous, such as during a pullback procedure. Physiological measurements can occur while the intravascular device is moved in one direction. Measurement collection can be discontinuous procedure, such as when the intravascular device is selectively moved through the vessel (e.g., when movement of the intravascular device starts and stops, when the intravascular device is held at various points along the vessel longer than others, etc.). Physiological measurements can occur while the intravascular device is moved in both directions (e.g., proximally and distally within the blood vessel). Co-registration can be used to ensure that, regardless of how the physiological measurements were collected, the location of the measurement can be identified on an angiographic image of the vessel. For example, a composite of the collected physiological measurements can be generated based on the co-registered data.

In that regard, in some instances the pressure measurements are representative of a pressure ratio between a fixed location within the vessel and the moving position of the instrument as the instrument is moved through the vessel. For example, in some instances a proximal pressure measurement is obtained at a fixed location within the vessel while the instrument is pulled back through the vessel from a first position distal of the position where the proximal pressure measurement is obtained to a second position more proximal than the first position (i.e., closer to the fixed position of the proximal pressure measurement). For clarity in understanding the concepts of the present disclosure, this arrangement will be utilized to describe many of the embodiments of the present disclosure. However, it is understood that the concepts are equally applicable to other arrangements. For example, in some instances, the instrument is pushed through the vessel from a first position distal of the proximal pressure measurement location to a second position further distal (i.e., further away from the fixed position of the proximal pressure measurement). In other instances, a distal pressure measurement is obtained at a fixed location within the vessel and the instrument is pulled back through the vessel from a first position proximal of the fixed location of the distal pressure measurement to a second position more proximal than the first position (i.e., further away from the fixed position of the distal pressure measurement). In still other instances, a distal pressure measurement is obtained at a fixed location within the vessel and the instrument is pushed through the vessel from a first position proximal of the fixed location of the distal pressure measurement to a second position less proximal than the first position (i.e., closer the fixed position of the distal pressure measurement).

In typical embodiments, a processing system can collect raw pressure data from the intravascular device and process the data to compute pressure differential(s) or ratio(s). The pressure differential between the two pressure measurements within the vessel (e.g., a fixed location pressure measurement and a moving pressure measurement) is calculated as a ratio of the two pressure measurements (e.g., the moving pressure measurement divided by the fixed location pressure measurement), in some instances. In some instances, the pressure differential is calculated for each heartbeat cycle of the patient. In that regard, the calculated pressure differential is the average pressure differential across a heartbeat cycle in some embodiments. For example, in some instances where a hyperemic agent is applied to the patient, the average pressure differential across the heartbeat cycle is utilized to calculate the pressure differential. In other embodiments, only a portion of the heartbeat cycle is utilized to calculate the pressure differential. The pressure differential is an average over the portion or diagnostic window of the heartbeat cycle, in some instances.

In some embodiments a diagnostic window is selected using one or more of the techniques described in U.S. patent application Ser. No. 13/460,296, filed Apr. 30, 2012 and titled "DEVICES, SYSTEMS, AND METHODS FOR ASSESSING A VESSEL," which is hereby incorporated by reference in its entirety. As discussed therein, the diagnostic windows and associated techniques are particularly suitable for use without application of a hyperemic agent to the patient. In general, the diagnostic window for evaluating differential pressure across a stenosis without the use of a hyperemic agent is identified based on characteristics and/or components of one or more of proximal pressure measurements, distal pressure measurements, proximal velocity measurements, distal velocity measurements, ECG waveforms, and/or other identifiable and/or measurable aspects of vessel performance. In that regard, various signal processing and/or computational techniques can be applied to the characteristics and/or components of one or more of proximal pressure measurements, distal pressure measurements, proximal velocity measurements, distal velocity measurements, ECG waveforms, and/or other identifiable and/or measurable aspects of vessel performance to identify a suitable diagnostic window.

Figure 6:
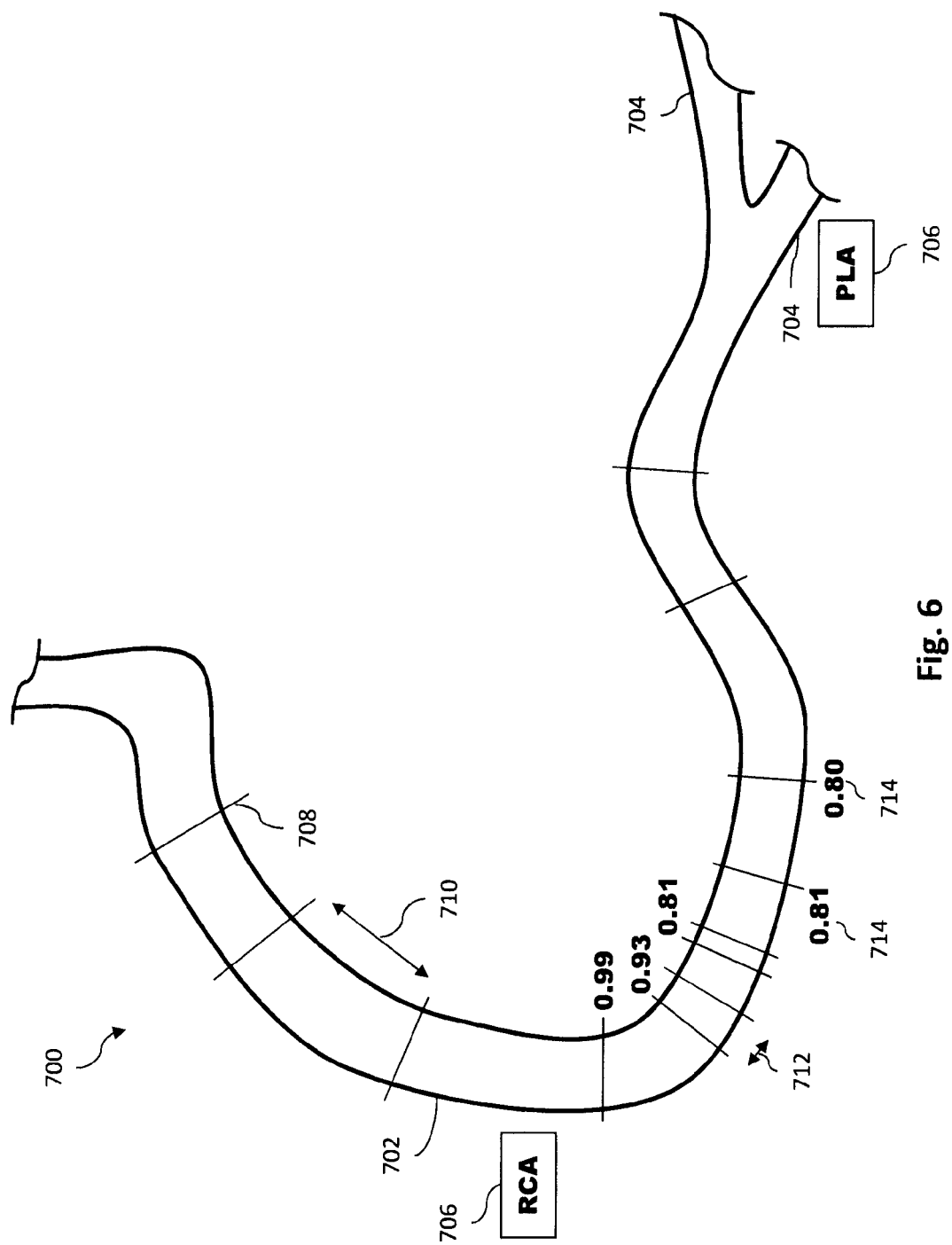
FIG. 6 is a screen display according to an embodiment of the present disclosure.
Figure 7:
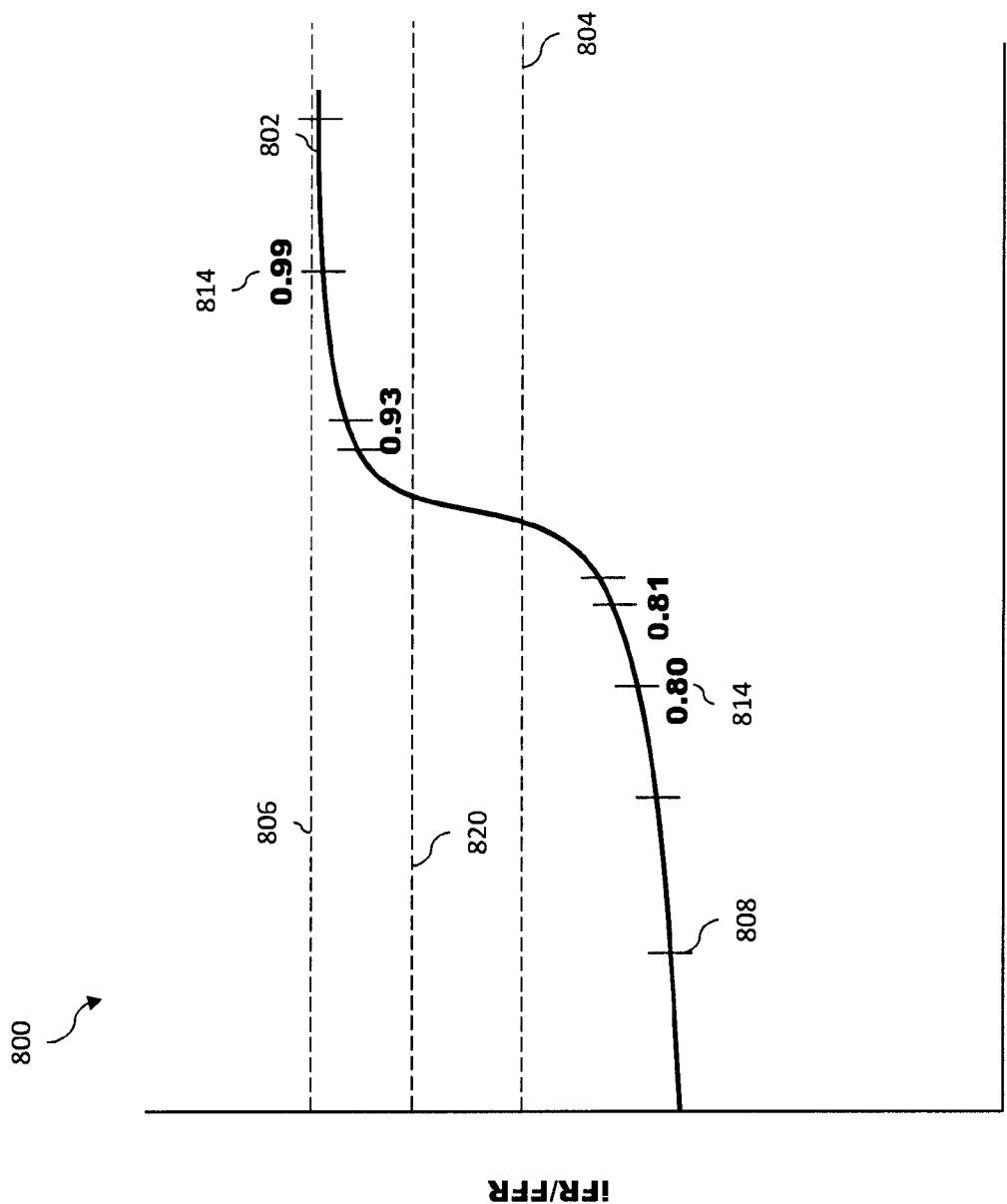
FIG. 7 is a screen display according to another embodiment of the present disclosure.
Figure 8:
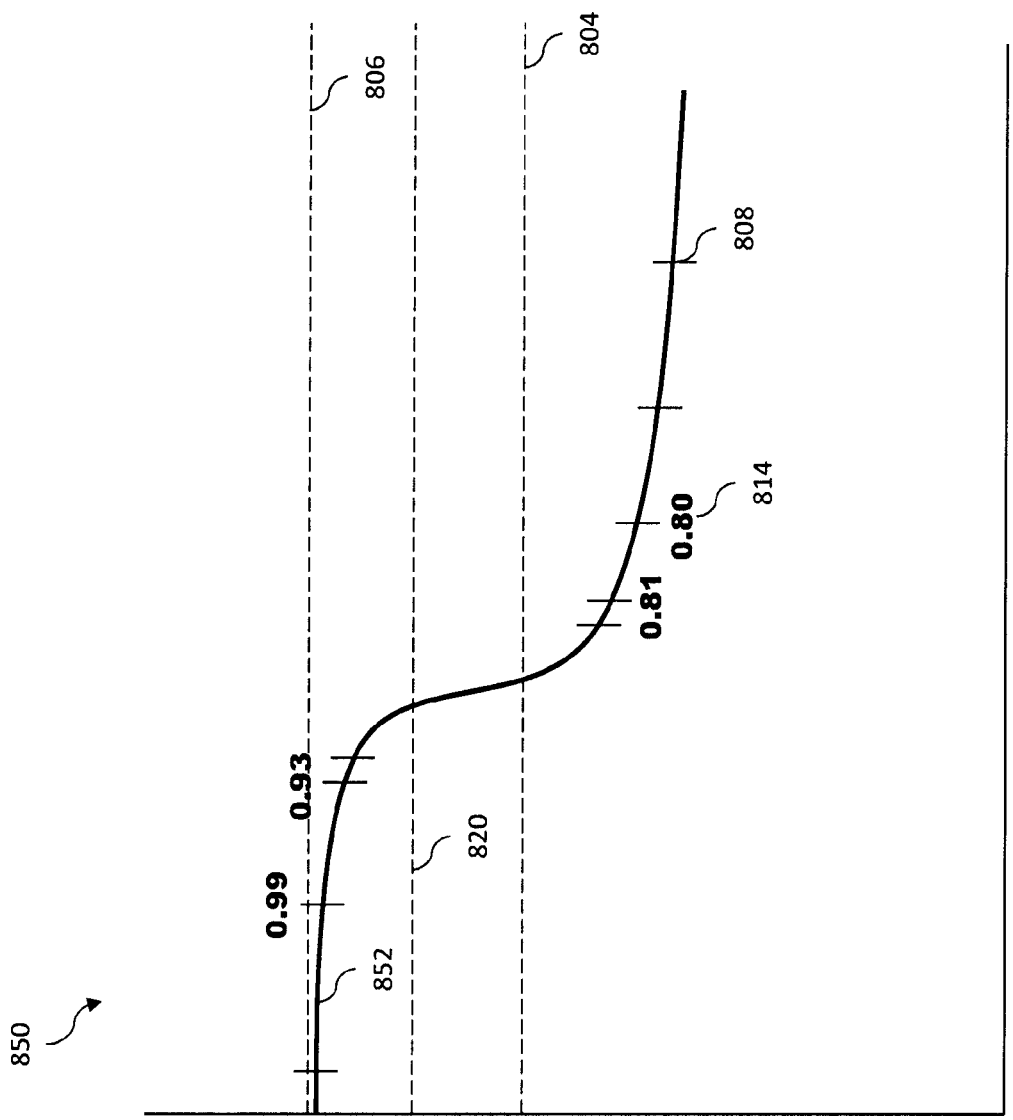
FIG. 8 is a screen display according to another embodiment of the present disclosure.

Referring now to FIGS. 6-8, the processing system can generate a screen display including the pressure measurements and/or pressure ratios at their associated locations based on the data obtained during blocks 510 and 520. For example, FIG. 6 illustrates a screen display 700 (or partial screen display) including a visual representation of a vessel. The screen display includes a visual representation of a vessel 702 into which an intravascular device having a pressure sensing component is guided. Angiographic and pressure data can be collected with the intravascular device within the vessel 702. For example, the pressure data can be collected during a pullback procedure, which in the embodiment of FIG. 6 is from the right to the left of the vessel 702. The collected angiography data can be used to generate an angiographic image including the vessel 702 and other branch vessels 704. The one or more visualizations described herein can be a graphical overlay on the angiographic image. The screen display 700 includes label fields 706 identifying the particular vessel(s). In some embodiments, a computing device (e.g., computing device 172 of FIG. 4) uses the angiography data, such as the contours, location, branches, and other features of the vessel(s) to automatically identify the vessel. The position and/or viewing angle of the external imaging system (e.g., angiography or x-ray system) can also be used to identify the vessel. A computing device can generate the display data associated with the labels 706, including alphabetical, numerical, alphanumeric, and/or symbolic characters. In the embodiment of FIG. 7, the labels 706 include an abbreviation of the identified vessel, such as "RCA" for right coronary artery and "PLA" for postero-lateral artery. While abbreviations and particular vessels are used in FIG. 7, it is understood that any suitable label can be used. In some embodiments, a user can selectively activate or deactivate one or more of the labels 706 such that a portion, all, or none of the labels 706 are included in the screen display 700.

The screen display 700 also includes markers 708 indicative of a location within the vessel 702 associated with the collected pressure measurements or computed pressure ratio. For example, the markers 708 can be a location of the pressure sensor when the pressure measurements are collected. In the embodiment of FIG. 6, the markers 708 are line segments that transect the vessel 702. Other examples of markers indicative of location are described in U.S. Provisional Application No. 61/895,909, titled "Devices, Systems, and Methods for Vessel Assessment," and filed Oct. 25, 2013, the entirety of which is hereby incorporated by reference herein. In one embodiment, such as during an iFR procedure, one pressure ratio is computed per heartbeat cycle. Thus, each marker 708 is indicative of collected data and/or computed pressure ratio during the heartbeat cycle. In some embodiments, a user can selectively activate or deactivate one or more of the markers 708 such that a portion, all, or none of the markers 708 are included in the screen display 700. The markers 708 can be separated by varying distances within the vessel 702, as indicated by distances 710 and 712. In turn, the distances 710 and 712 can correspond to the speed through which the pressure sensing device is guided through the vessel 702. In embodiments in which the pressure sensing device is guided through the vessel 702 at a constant speed, the distance between the markers 708 is equal or nearly equal such that successive markers 708 are positioned at equal or nearly equal intervals. In the embodiments in which the pressure sensing device is guided through the vessel 702 at a non-constant speed, the distance between the markers 708 will vary to a greater extent such that successive markers 708 are positioned at unequal intervals. For example, the pressure sensing device can be slowed down near an obstruction such that data from a relatively greater number of heartbeat cycles is collected. As illustrated in FIG. 6, there is less distance between successive markers 708 around a pressure change attributable to an obstruction in the vessel 702. Co-registration can be implemented such that the location of the pressure sensing intravascular device within the vessel 702 is known during each heartbeat cycle. As a result, the pressure sensing intravascular device can be guided through the vessel 702 (e.g., during a pullback procedure) with a non-constant speed such that the pace of data collection in the vessel 702 can be controlled by the clinician. For example, the clinician can slow down for more information near a clinically significant portion of the vessel 702 such as a lesion. For example, the clinician can speed up through non-clinically significant portions of the vessel 702.

The pressure change in the vessel 702 is indicated by the pressure ratio fields 714. The pressure ratio fields are provided adjacent the markers 708. In the embodiment of FIG. 6, only a portion of the pressure ratio fields 714 are shown. In various embodiments, a portion, all, or none of the pressure ratio fields 714 can provide the computed pressure ratio associated with a given location. For example, a user can selectively activate or deactivate one or more of the pressure ratio fields 714. In various embodiments, the pressure ratio fields 714 include alphabetical, numerical, alphanumeric, and/or symbolic characters. In FIG. 6, the fields 714 include are numeric values associated with an iFR calculation. In other embodiments, the fields 714 can include an FFR, iFR, Pd/Pa, compensated Pd/Pa, or other label to identify the type of quantity being displayed. Such embodiments are described, for example, in U.S. Provisional Application No. 61/895,909, titled "Devices, Systems, and Methods for Vessel Assessment," and filed Oct. 25, 2013, the entirety of which is hereby incorporated by reference herein. A pressure change is indicated by the values in the fields 714. For example, in FIG. 6, an obstruction in the vessel 702 likely exists between the values 0.93 and 0.81.

FIGS. 7 and 8 illustrate screen displays 800 and 850 (or partial screen displays) including a visual representation of a pressure ratio. The data depicted in the screen displays 800 and 850 of FIGS. 7 and 8, respectively, correspond to the data shown in screen display 700 of FIG. 6. The screen displays 800 and 850 include curves 802, 852 respectively of the pressure ratios within the vessel 702. The curves 802, 852 are representative of the same data, except that the x-axes are different. The screen display 800 (FIG. 7) includes time or distance on the x-axis and a pressure ratio quantity (such as iFR, FFR, Pd/Pa, etc.) on the y-axis. For example, in the embodiment shown in FIG. 6, a moving pressure sensing device can be guided from right to left within the vessel 702 during the pullback procedure while a fixed pressure sensing device remains stationary on the left side or proximal portion of the vessel 702. Values along the x-axis of screen display 800 can correspond to the duration of a pullback procedure and/or distance traveled by the moving pressure sensing device during the pullback procedure. The screen display 850 includes position corresponding to the physical orientation of the vessel 702 along the x-axis and a pressure ratio quantity (such as iFR, FFR, Pd/Pa, etc.) on the y-axis. That is, the screen display 850 shows the pressure ratios associated with the left side of the vessel 702 on the left side of the curve 852 and the pressure ratios associated with the right side of the vessel 702 on the right side of the curve 852. In some instances, providing a pressure ratio plot that corresponds to the physical location along the vessel can facilitate easier PCI planning for a user. The discussion below generally refers to the screen display 850, but it is understood that the screen display 800 can be equivalently utilized.

The screen displays 800 and 850 include an ideal pressure ratio line 806. The ideal line 806 is representative of a pressure ratio equal to one (1), which is indicative of a vessel with no obstructions. Physiologically, a pressure ratio equal to one (1) is the maximum possible pressure ratio and occurs when proximal and distal pressure measurements are equal. During PCI planning, a clinician tries to determine treatment parameters that will cause a patient's pressure ratios to return as closely as possible to the ideal line 806.

The screen displays 800 and 850 include a threshold pressure ratio 804. The threshold 804 can be set at a value indicative of transition between pressure ratios representative of a healthy vessel and pressure ratios representative of a vessel having a significant obstruction. Pressure ratios above the threshold 804 can be representative of a vessel for which treatment is not recommended, and pressure ratios below the threshold 804 can be representative of a vessel for which treatment is recommended. The threshold 804 can vary depending on the pressure ratio scale (e.g., iFR, FFR, Pd/Pa, etc.) used in the screen displays 800 and 850. For example, the threshold 804 for FFR can be 0.80, and the threshold 804 for iFR can be 0.89. For example, if a vessel has FFR values above 0.80, the clinician can determine not to treat the vessel. If the vessel has FFR values below 0.80, the clinician can determine to treat the vessel with a PCI. In some instances the threshold values are set empirically. In other instances, the threshold values are set, at least partially, based on user preference/selection.

The screen displays 800 and 850 include a target line 820. The target line 820 can correspond to a pressure ratio value that is associated with clinically beneficial outcomes for the patient. The target line 820 can correspond to a pressure ratio value higher than the threshold 804 in some embodiments. That is, the threshold 804 can represent a minimum pressure ratio value that can be considered healthy, while the target line 820 can represent a higher pressure ratio value that is associated with efficacious treatment. The target line 820 can vary depending on the pressure ratio scale (e.g., iFR, FFR, Pd/Pa, etc.) used in the screen displays 800 and 850. For example, the target line 820 for FFR can be 0.93. The graphical user interface for PCI planning can allow the clinician to set the pressure ratio value for the threshold 804 and/or the target line 820. For example, the clinician can access settings options that allow for modification of the threshold 804 and/or the target line 820. It is desirable to return the actual pressure ratio values of the curves 802 and 852 to the value indicated by the ideal line 806. However, it may not be medically possible to recreate perfect flow within a stenosed vessel for a variety of reasons. In such circumstances, the target line 820 represents a medically acceptable pressure ratio values that are indicative of efficacious treatment. In some instances, the target line 820 is a desired outcome set by the user from which the system identifies available treatment options for achieving the pressure ratio values satisfying the target line 820. Thus, during PCI planning, the system can determine treatment parameters to return the patient's pressure ratio values to as close to the ideal line 806 as possible and at least above the target line 820. The threshold 804, the target line 820, and/or the ideal line 806 can be selectively provided on the screen displays 800 and 850, in response to a user input to show/hide the visualizations. In that regard, it is understood that none or any one or more the threshold 804, the target line 820, and/or the ideal line 806 can be provided on the screen displays.

In some embodiments, various colors and/or other visual indicators are provided on the screen displays 800 and 850 to indicate a difference between the threshold 804 and the actual pressure ratio. For example, a first color (e.g., green, white, or otherwise) can be utilized to represent values well above the threshold value (e.g., where the threshold value is 0.80 on a scale of 0.00 to 1.00, values above 0.90), a second color (e.g., yellow, gray, or otherwise) can be utilized to represent values near but above the threshold value (e.g., where the threshold value is 0.80 on a scale of 0.00 to 1.00, values between 0.81 and 0.90), and a third color (e.g., red, black, or otherwise) can be utilized to represent values equal to or below the threshold value (e.g., where the threshold value is 0.80 on a scale of 0.00 to 1.00, values of 0.80 and below). It is appreciated that any number of color combinations, scalings, categories, and/or other characteristics can be utilized to visually represent the relative value of the pressure differential to the threshold value. However, for the sake of brevity Applicants will not explicitly describe the numerous variations herein.

The screen displays 800 and 850 additionally include markers 808 and pressure ratio fields 814. The markers 808 and pressure ratio fields 814 are similar to those described in the context of FIG. 6. While the curves 802 and 852 are depicted as continuous in FIGS. 7 and 8, the markers 808 can be representative of actual data points on the curves 802 and 852. The values of the curves 802 and 852 between the markers 808 can be interpolated based on the pressure ratios associated with the markers 808. A computing device (e.g., computing device 172 of FIG. 4) can provide data processing, data interpolation, smoothing, and perform other computations to generate the pressure ratio curves 802 and 852. The ideal pressure ratio line 806, the threshold 804, markers 808, and pressure ratio fields 814 can be selectively activated and deactivated such that a portion, all, or none appear the screen displays 800 and 850.

At block 530, the method 500 includes receiving a user input (or multiple user inputs) regarding a desired outcome. In this regard, the desired outcome can be a desired and/or minimum pressure ratio (e.g., iFR, FFR, Pd/Pa, etc.) at one or more positions along the length of the vessel. For example, in some instances a user may input an overall desired pressure ratio for the vessel (e.g., iFR≥0.93). Further, in some instances a user may input a desired pressure ratio for multiple locations along the length of a vessel (e.g., location 1: iFR≥0.96, location 2: iFR≥0.95, location 3: iFR≥0.93, etc.). To this end, a user interface may display the vessel and/or a graphical representation of the pressure measurements/ratios to allow a user to visualize the locations of the desired outcome(s) relative to the current state of the vessel. Further, the user interface can include buttons, input fields, toggles, sliders, and/or other interface mechanisms to allow the user to input the desired outcome (e.g., target and/or minimum pressure ratios) and/or the respective location(s) for the desired outcome. Also, the user interface may allow the user to select what treatment options should be considered for a patient. For example, in some instances the user may select one or more of stenting, angioplasty, bypass, ablation, pharmaceutical, other treatment options, and/or combinations thereof. For example, each of FIGS. 9-12 illustrates an exemplary approach where a user input box 880 is provided in the upper right hand corner of each display. As shown, the illustrated user input box 880 allows a user to specify a desired iFR/FFR value, specify a minimum iFR/FFR value, and select the available treatment options for consideration by the system for treatment planning purposes.

Referring again to FIG. 5, at block 540, the method 500 includes conducting treatment planning to identify one or more suitable treatment options for achieving the desired outcome of block 530. For example, the treatment planning can include determining which of the available treatment options is best suited to achieve the desired outcome. The processing system can make this determination by utilizing empirical data of the treatment of previous patients with similar symptoms and treatment(s), expected effect of treatment (e.g., as stated by the manufacturer/supplier of the treatment, as defined by the user, as established by empirical treatment data, and/or combinations thereof), and/or combinations thereof. In some embodiments, the treatment planning includes having a computing device (e.g., computing device 172) of the system determine one or more recommended characteristics of a stent, angioplasty balloon, ablation area, and/or other treatment option to be deployed within the vessel 702. For example, for a stent deployment, the computing device may determine suitable/desired position, diameter, length, material, etc. for one or more stent locations. For angioplasty, the computing device may determine suitable/desired position(s), balloon size (length, inflated diameter), balloon material, etc. for one or more angioplasty locations. For ablation, the computing device may determine suitable/desired ablation type (e.g., laser, ultrasound, cryo, etc.), position(s), amount of material to be removed, etc. for one or more ablation locations. The determination of the one or more characteristics of the different treatment types can be based on the collected pressure data, computed pressure ratio(s), angiography data, a threshold pressure ratio, a target pressure ratio, an ideal pressure ratio, etc. For example, the characteristics of the treatment(s) can be selected to remedy a drop in the pressure ratio across an obstruction. The computing device can determine the suitable/desired characteristics of the treatment option(s) and identify the available and/or recommended treatment option(s).

At block 550, the method 500 includes outputting a screen display that includes a visual representation of the one or more suitable treatments identified during the treatment planning at block 540. For example, as shown in FIGS. 9-12, the screen display can include visualizations based on the pressure measurements and/or a visual representation of the vessel along with the recommended treatment option(s). In some embodiments, the visual representation of the vessel is a two-dimensional or three-dimensional angiographic image of the vessel, such as an angiographic image generated based on angiography data collected at block 520. In some embodiments, visual representation of the vessel is two-dimensional or three-dimensional graphical representation of the vessel, such as a stylized image or reconstruction of the vessel. The visualization based on the pressure measurements can include numerical, graphical, textual, and/or other suitable visualizations based on the pressure data collected at block 510. Collectively, the visualizations can include one or more of treatment overlaid onto the visual representation of the vessel, calculated pressure ratio(s), markers indicative of a location within the vessel of the obtained pressure measurements or the calculated pressure ratio(s), a label identifying the vessel, among others. In some embodiments, the visualization based on the pressure measurements can include a heat map in which the visual representation of the vessel is colorized or otherwise gradated to shows changes in the obtained pressure measurements or calculated pressure ratio(s). Examples of screen displays including a heat map, calculated pressure ratios, markers indicative of a location associated with the obtained pressure measurements or the calculated pressure ratios, and other visualizations are described in U.S. Provisional Application No. 61/895,909, titled "Devices, Systems, and Methods for Vessel Assessment," and filed Oct. 25, 2013, the entirety of which is hereby incorporated by reference herein. In various embodiments, other collected data, computed quantities, etc., such as ECG waveforms, numerical values, can be provided on the screen display as described in U.S. Provisional Application No. 62/049,265, titled "Bedside Controller for Assessment of Vessels and Associated Devices, Systems, and Methods," and filed Sep. 11, 2014, the entirety of which is hereby incorporated by reference herein.

Figure 9:
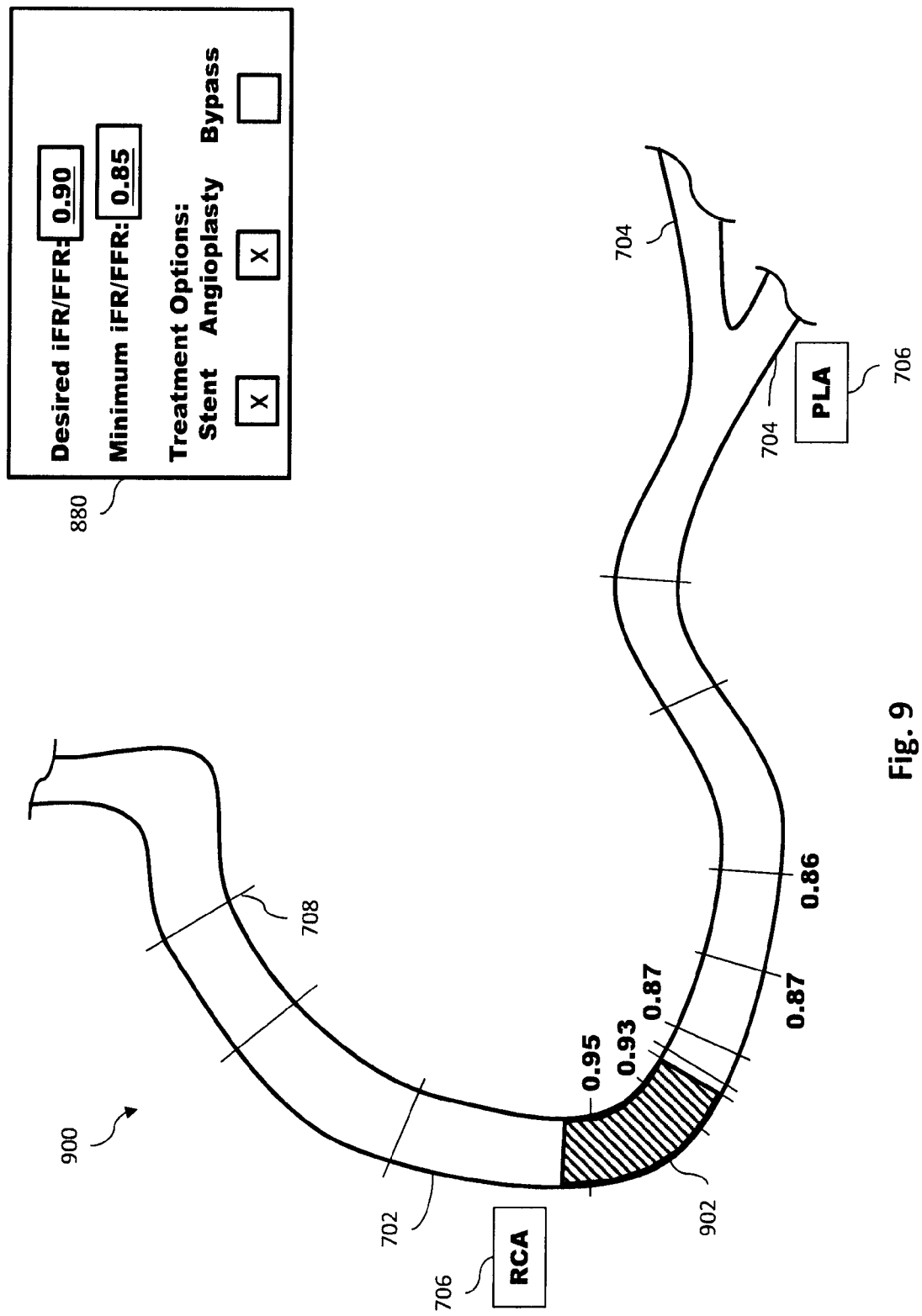
FIG. 9 is a screen display according to another embodiment of the present disclosure.
Figure 10:
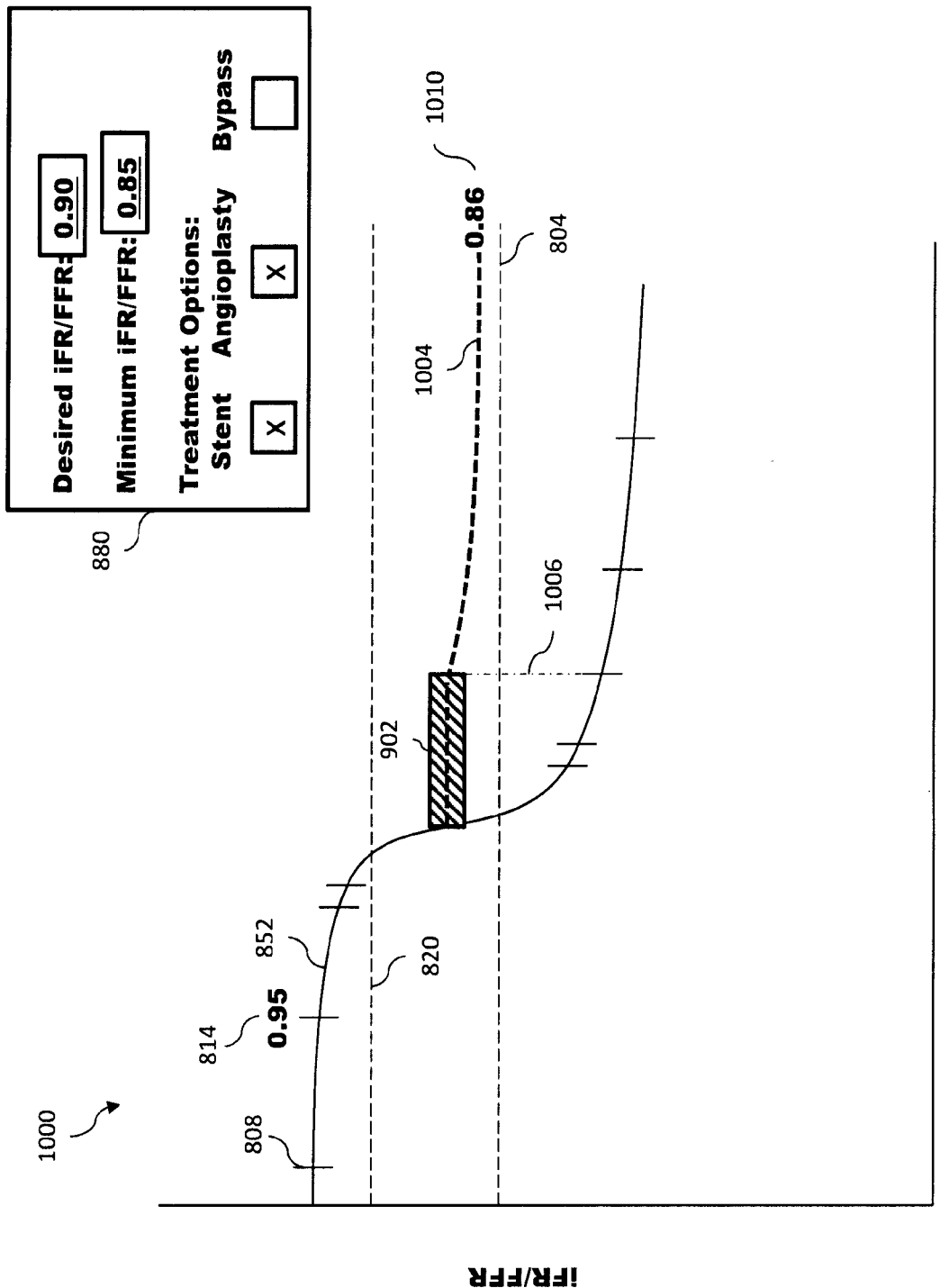
FIG. 10 is a screen display according to another embodiment of the present disclosure.

Referring more specifically to FIGS. 9 and 10, shown therein are examples of screen displays illustrating a treatment option identified in block 540. In this regard, the data and treatment option depicted in the screen display 900 (FIG. 9) corresponds to the data shown in screen display 1000 (FIG. 10). In particular, a graphical representation of a stent 902 is positioned in the visual representation of the vessel 702. For clarity purposes, the following discussion focuses on a stent treatment. However, it is understood that the same concepts apply to other treatment options including, angioplasty, ablation, bypass, etc. The stent 902 can be inserted into or overlaid onto the image of the vessel in response to system identifying the stent 902 as the best treatment option based on the analysis at block 540. As described above, the location, length, diameter, material, and/or other characteristics of the stent 902 can be automatically determined by a computing device and correspondingly displayed on the screen display 900 at the location of deployment. For example, the diameter of the stent can be auto-sized to match the diameter of the vessel in the angiographic image. The image characteristics of the stent 902 that determine how the stent 902 appears in the screen display 900 can be chosen such that the stent 902 is visually distinguishable within the vessel 702. The image characteristics can include a color, shading, pattern, transparency, borders, and other related characteristics. In some embodiments, the image characteristics of the stent 902 are selected to match the physical appearance of an actual stent. In some embodiments, the image characteristics of the stent 902 are selected to highlight a region within the vessel 702 in which the stent is inserted. Further, estimated physiologic values (e.g., iFR, FFR, Pd/Pa, etc.) associated with deployment of the stent within the vessel 702 can be determined by the system based on the location, length, diameter, material, and/or other virtual/simulated characteristics of the stent 902. The estimated physiologic values can be displayed on the screen display to show the physiologic change caused by deployment of the stent (or other treatment). For example, in some instances FIG. 9 can be considered an updated version of FIG. 6 showing the position of the stent 902 within the vessel and the estimated pressure ratio values associated with the treatment. In some instances, the original pressure ratio values may be displayed alongside the estimated pressure ratio values so that a user can see the estimated effects of the treatment.

FIG. 10 illustrates a screen display 1000 (or partial screen display) including a visual representation of a pressure ratio.

The data depicted in the screen display 1000 (FIG. 10) corresponds to the data shown in screen display 900 (FIG. 9). A graphical representation of the stent 902 is positioned along the visual representation of the pressure ratio curve 852. The characteristics of the graphical representation of stent 902, such as the position and length, among others, correspond to the characteristics of the graphical representation of stent 902 that is positioned within the vessel 702 (FIG. 9). The screen display 1000 (FIG. 10) includes corrected pressure curve 1004. The corrected pressure curve 1004 represents the anticipated changes to pressure curve 852 as a result of the deployment of the stent 902. No change in the pressure is expected across the length of the stent 902, as illustrated in the corrected pressure curve 1004. That is, placement of the stent 902 is ideally creating perfect or near perfect flow across that portion of the vessel 702. An end of the stent 902 can be indicated by a stent end notation 1006. In different embodiments, various other graphical representations of the stent end can be utilized. The stent end notation 1006 can be selectively provided to the screen display 1000, e.g., based on a user input to show/hide the visualization. The stent end notation 1006 is representative of the point beyond which the corrected pressure curve 1004 is expected to behave like the pressure curve 852. As shown, the corrected pressure curve 1004 is shaped similar to the pressure curve 852, past the stent end notation 1006. However, the pressure values indicated by the corrected pressure curve 1004 are higher as a result of the stent 902 correcting at least a portion of the pressure drop across a lesion in the vessel. Similar display approaches can be used to visualize the effects of other treatment options identified at block 540, including angioplasty, ablation, bypass, etc.

Screen display 1000 additionally includes a corrected pressure ratio value 1010. The corrected pressure ratio value 1010 can correspond to the numerical value of the corrected pressure ratio curve 1004. One or both of the corrected pressure ratio value 1010 and the corrected pressure ratio curve 1004 can provide a clinician validation that the selected treatment will achieve the target and/or minimum pressure ratio values set by the user as the desired outcome for the patient. For example, the threshold 804 can correspond to an iFR value of 0.89, above which vessels can be characterized as healthy. If the corrected pressure ratio value 1010 provides an iFR value that is greater than 0.89 (as it does in the embodiment of FIG. 10), the clinician can understand that the placement of the stent with the given parameters (e.g., length, diameter, position, etc.) will provide some benefit in treating the vessel. The corrected pressure ratio value 1010 can be associated with the distal portion of the corrected pressure ratio curve 1004 (e.g., the distal most value, an average of values of the corrected pressure ratio curve, etc.). The corrected pressure ratio value 1010 can be provided adjacent corrected pressure ratio curve 1004. The corrected pressure ratio value 1010 can be selectively provided in response to a user input to show/hide the visualization.

A computing device (e.g., computing device 172) can compute the values of the corrected pressure curve 1004 based on the obtained pressure measurements, calculated pressure ratios, target pressure ratio, ideal pressure ratio, etc. The corrected pressure curve 1004 can be computed and provided to the user such that the curve 1004 is adjusted based on the treatment(s) identified in block 540. In this regard, the system can modify the characteristics of the treatment(s) so that the values of the corrected pressure curve are as close to being equal to an ideal pressure ratio (such the ideal pressure ratio line 806 of FIG. 8) and/or at least greater than a target pressure ratio (such as the target line 820 of FIG. 8).

Figure 11:
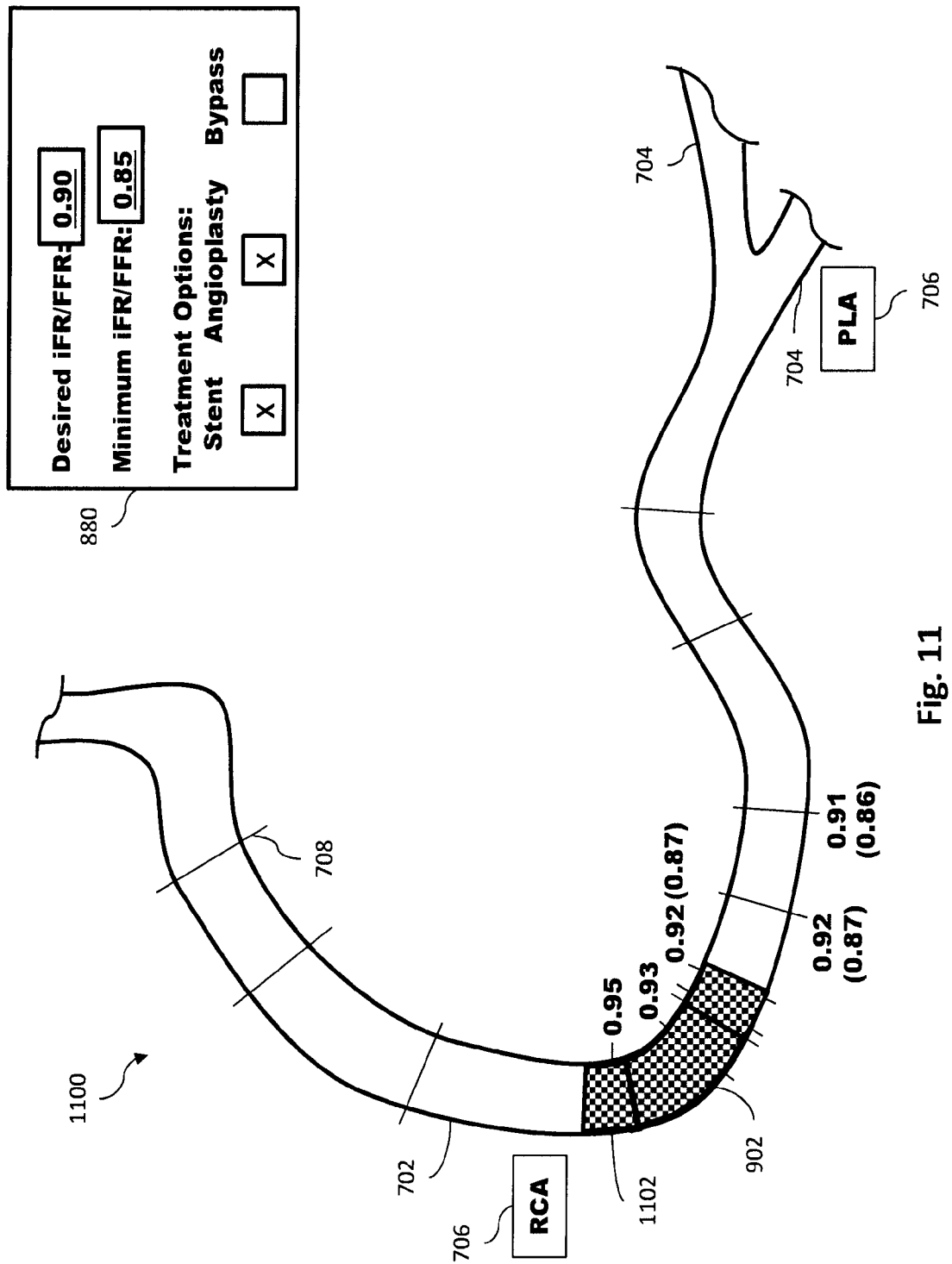
FIG. 11 is a screen display according to another embodiment of the present disclosure.
Figure 12:
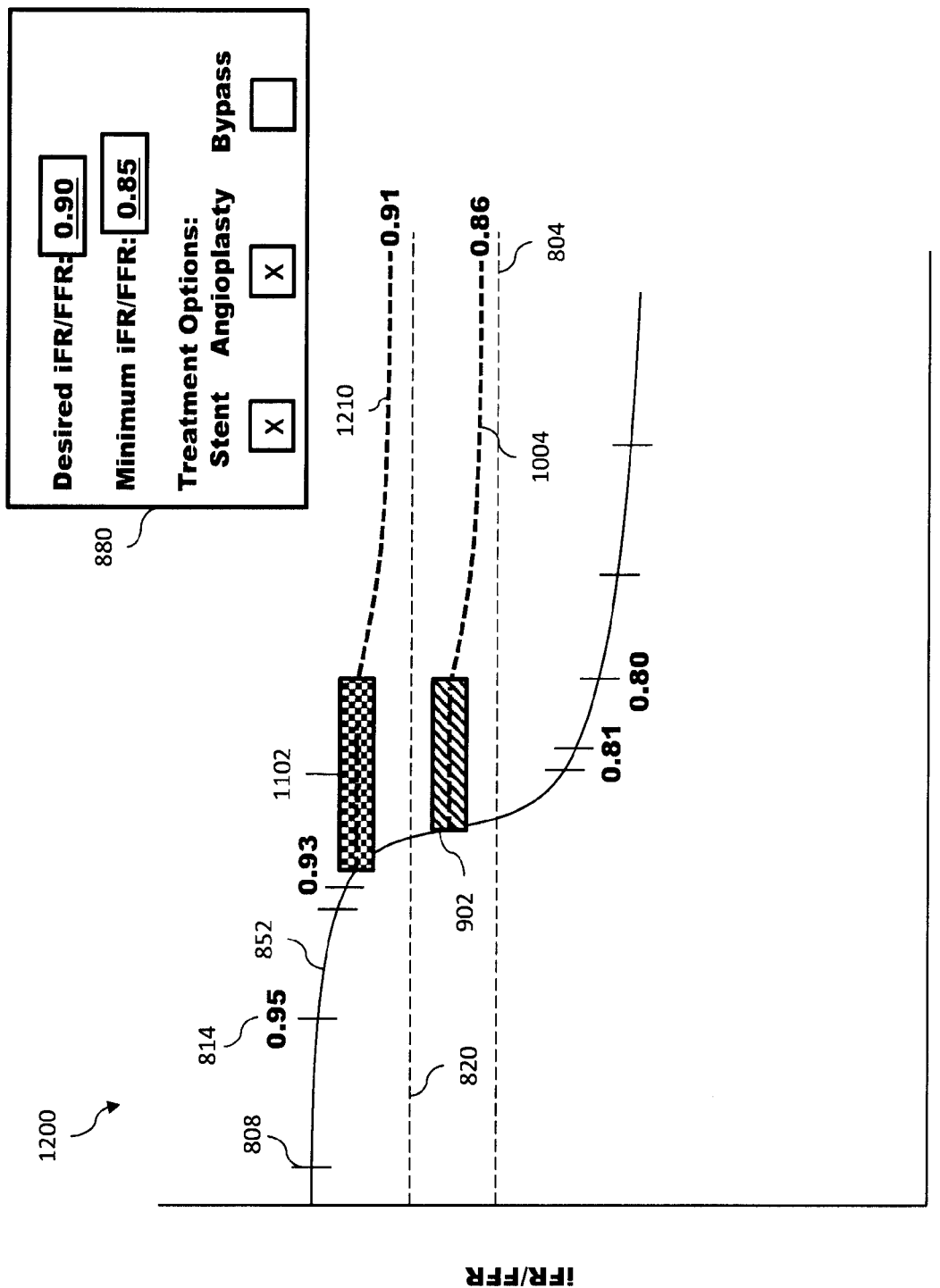
FIG. 12 is a screen display according to another embodiment of the present disclosure.

FIGS. 11 and 12 are similar in many respects to FIGS. 9 and 10, but each show two identified treatment options and the corresponding effects to the pressure ratios. For example, FIGS. 11 and 12 each show a first treatment option (stent 902) and a second treatment option (1102) and the corresponding estimated effects to the pressure ratio. As shown, each of the treatment options (stents 902 and 1102) satisfy the threshold line 804, but only the second treatment option (stent 1102) satisfies the target line 820. However, there may be situations where the second treatment option (stent 1102) is not available and/or advisable for one reason or another (e.g., the stent 1102 is not in inventory, stent 1102 is not advisable due to another patient characteristic, etc.) such that the first treatment option (stent 902) is the best available treatment option.

At block 560, a treatment option is selected for implementation from the one or more suitable treatments identified during the treatment planning. In this regard, a user can select the best available treatment from the identified treatment options based on the visualizations of the treatment options (e.g., as shown in FIGS. 9-12), user experience, and/or other factors. Further, in some instances, at block 560 the method 500 includes receiving a user input to modify one or more features of the treatment option(s) identified by the system at block 540 to select a treatment option for implementation. The user input can be to insert a stent into the visual representation of the vessel and/or move the stent within the vessel. The user input can be to change one or more characteristics of the stent, such as length, diameter, material, etc. For example, the user input can be to increase or decrease the length of the stent within the vessel. The user input can be received at a user interface device. In some embodiments, the user input is a touch input received at a touch sensitive display of a bedside controller. The screen display can be updated to reflect the changes to the treatment option(s) based on the user input. For example, in response to the user input, a stent can be inserted into the visual representation of the vessel, the location of the stent within the vessel can be changed, and one or more characteristics of the stent (e.g., length, diameter, material, etc.) can be changed. The estimated pressure ratio values can also be updated based on the changes to the proposed treatment options.

In some instances, the clinician can decide that none of the identified treatment options are suitable for implementation. For example, even the best treatment option(s) identified by the system do not result in the corrected pressure ratio curve 1004 or the corrected pressure ratio value 1004 equaling or exceeding the target line 820, at which clinical benefits are likely to result from the therapeutic intervention. In such instances, no treatment option is selected at block 560 and the method 500 can return to block 530, as indicated by line 565. At block 530, the clinician can then vary the desired outcome(s) and/or available treatment options for the system to select from to broaden the available treatment options in an effort to identify an suitable treatment option. The method can then proceed to block 540 and continue until a suitable treatment option is identified.

At block 570, the method 500 includes performing the treatment option selected at block 560.

At block 580, the method 500 includes verifying the desired outcome has been achieved by performing the selected treatment option. For example, where the desired outcome was achieving a minimum pressure ratio, pressure measurements can be obtained after performing the selected treatment to determine whether the minimum pressure ratio has been achieved. If minimum pressure ratio has been achieved, then the treatment is considered successful and the clinician can conclude the treatment. If the minimum pressure ratio has not been achieved, then the clinician can verify that the treatment was performed properly (e.g., confirm that the stent is fully deployed) and/or evaluate what steps should be taken next, which can include additional diagnosis/treatment or concluding the treatment with the current results. In some instances, the method 500 is repeated to identify a further treatment option if the desired outcome has not been achieved with the treatment option performed at block 570.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

The invention claimed is:

1. An intravascular processing system for evaluating a vessel of a patient, comprising:
a processing system communicatively coupled to one or more intravascular pressure-sensing devices and a display device, the processing system configured to:
receive pressure measurements obtained by the one or more intravascular pressure-sensing devices positioned within the vessel of the patient;
output, to the display device, a screen display comprising a desired pressure field, a minimum pressure field, and a treatment option field;
receive, via the desired pressure field, a first user input indicating a desired pressure value for the vessel;
receive, via the treatment option field, a second user input selecting a set of treatment options;
determine, responsive to the second user input and based on the received pressure measurements, a respective corrected pressure value for the vessel resulting from each treatment option of the set of treatment options;
identify one or more treatment options of the set of treatment options based on the respective corrected pressure value corresponding to the one or more treatment options satisfying a minimum pressure value; and
update the screen display output to the display device to evaluate the one or more treatment options, the updated screen display including:
a visual representation of the desired pressure value;
a visual representation of a minimum pressure value associated with the minimum pressure field;
a visual representation of the one or more treatment options; and
a visual representation of the respective corrected pressure value corresponding to the one or more treatment options.

2. The system of claim 1, wherein the processing system is further configured to receive angiography data obtained simultaneously with the pressure measurements.

3. The system of claim 2, wherein the visual representation of the one or more treatment options includes a graphical overlay on an angiographic image based on the angiography data.

4. The system of claim 1, wherein the received pressure measurements include proximal pressure measurements and distal pressure measurements, and wherein the desired pressure value is a pressure ratio.

5. The system of claim 1, wherein the second user input comprises a selection of one or more treatment types corresponding to the set of treatment options.

6. The system of claim 5, wherein the one or more treatment types include at least one of an angioplasty, a stent, a coronary artery bypass graft, an ablation, or a pharmaceutical.

7. The system of claim 1, wherein, responsive to the second user input indicating a stent, the processing system is configured to identify the one or more treatment options further based on identifying a stent deployment location within the vessel.

8. The system of claim 7, wherein, responsive to the second user input indicating a stent, the processing system is configured to identify the one or more treatment options further based on identifying at least one stent parameter selected from the group consisting of stent length, stent diameter, and stent material.

9. The system of claim 1, wherein the processing system is configured to receive additional pressure measurements obtained by one or more intravascular pressure-sensing instruments positioned within the vessel of the patient after performance of at least one of the one or more treatment options.

10. The system of claim 9, wherein the processing system is configured to determine whether a pressure value based on the additional pressure measurements meets the desired pressure value for the vessel of the patient, wherein the desired pressure value is a threshold value for a pressure ratio of distal pressure measurements relative to proximal pressure measurements.

11. The system of claim 1, wherein the processing system is configured to:
receive, via the screen display, a user input to modify a characteristic of the one or more treatment options;
modify the visual representation of the one or more treatment options based on the characteristic; and
modify the visual representation of the respective corrected pressure value based on the modified corresponding one or more treatment options.

12. The system of claim 1, wherein:
the visual representation of the one or more treatment options comprises a representation of a first treatment option and a representation of a second treatment option; and
the visual representation of the respective corrected pressure value comprises a representation of a first corrected pressure value resulting from the first treatment option and a representation of a second corrected pressure value resulting from the second treatment option.

13. The system of claim 1, wherein the processing system is further configured to:
receive, via the screen display, a fourth user input selecting one of the one or more treatment options; and update the screen display output to the display device to include a visual representation of the selected one of the one or more treatment options.

14. The system of claim 1, wherein the processing system is further configured to:
receive, via the minimum pressure field, a third user input indicating the minimum pressure value.

* * * * *